United States Patent
Meng

(10) Patent No.: US 9,173,404 B2
(45) Date of Patent: *Nov. 3, 2015

(54) COMPOSITIONS COMPRISING AN ARYL PYRAZOLE AND A SUBSTITUTED IMIDAZOLE, METHODS AND USES THEREOF

(71) Applicant: MERIAL LIMITED, Duluth, GA (US)

(72) Inventor: Charles Q Meng, Johns Creek, GA (US)

(73) Assignee: MERIAL, INC., Duluth, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/358,309

(22) PCT Filed: Nov. 16, 2012

(86) PCT No.: PCT/US2012/065462
§ 371 (c)(1),
(2) Date: May 15, 2014

(87) PCT Pub. No.: WO2013/074892
PCT Pub. Date: May 23, 2013

(65) Prior Publication Data
US 2014/0303220 A1 Oct. 9, 2014

Related U.S. Application Data

(60) Provisional application No. 61/560,969, filed on Nov. 17, 2011.

(51) Int. Cl.
*A01N 43/56* (2006.01)
*A01N 43/50* (2006.01)
*C07D 233/58* (2006.01)
*A01N 47/02* (2006.01)
*A61K 31/415* (2006.01)
*A61K 31/4164* (2006.01)

(52) U.S. Cl.
CPC ................ *A01N 47/02* (2013.01); *A01N 43/50* (2013.01); *A01N 43/56* (2013.01); *A61K 31/415* (2013.01); *A61K 31/4164* (2013.01); *C07D 233/58* (2013.01)

(58) Field of Classification Search
None
See application file for complete search history.

(56) References Cited

U.S. PATENT DOCUMENTS 7,417,057 B2   8/2008   Dixson et al.

OTHER PUBLICATIONS

Prullage et al., The combined Mode of Action of Fipronil and Amitraz on the Motility of *Rhipicephalus sanguineus*, Apr. 8, 2011, pp. 302-310, vol. 179, No. 4, Vet. Parasitology.

*Primary Examiner* — Kamal Saeed
(74) *Attorney, Agent, or Firm* — Judy Jarecki-Black; John Ezcurra; Merial, Inc.

(57) ABSTRACT

This invention relates to compositions for combating parasites in animals, comprising 1-arylpyrazole compounds in combination with substituted imidazole compounds. This invention also provides for an improved methods for eradicating, controlling, and preventing parasite infestation in an animal comprising administering the compositions of the invention to an animal in need thereof.

16 Claims, No Drawings

COMPOSITIONS COMPRISING AN ARYL PYRAZOLE AND A SUBSTITUTED IMIDAZOLE, METHODS AND USES THEREOF

INCORPORATION BY REFERENCE

Any foregoing applications, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Citation or identification of any document in this application is not an admission that such document is available as prior art to the present invention.

FIELD OF THE INVENTION

The present invention provides veterinary compositions comprising 1-arylpyrazoles in combination with other active agents for eradicating ectoparasites or endoparasites; the use of these compositions against ectoparasites or endoparasites, and methods for preventing or treating parasitic infestations of animals comprising administering the inventive composition of the invention to the animal. In one embodiment, the combination is a 1-arylpyrazole with a substituted imidazole that exhibits improved stability, and a kit for treating or preventing parasitic infestations in animals, which comprises at least one 1-arylpyrazoles and at least one substituted imidazole in a single use container.

BACKGROUND OF THE INVENTION

Animals such as mammals and birds are often susceptible to parasite infestations/infections. These parasites may be ectoparasites, such as insects, and endoparasites such as filariae and other worms. Domesticated animals, such as cats and dogs, are often infested with one or more of the following ectoparasites:

fleas (*Ctenocephalides* spp., such as *Ctenocephalides* felts and the like),
ticks (*Rhipicephalus* spp., *Ixodes* spp., *Dermacentor* spp., *Amblyoma* spp., and the like),
mites (*Demodex* spp., *Sarcoptes* spp., *Otodectes* spp., and the like),
lice (*Trichodectes* spp., *Cheyletiella* spp., *Lignonathus* spp. and the like),
mosquitoes (*Aedes* spp., *Culux* spp., *Anopheles* spp. and the like) and
flies (*Hematobia* spp., *Musca* spp., *Stomoxys* spp., *Dematobia* spp., *Coclyomia* spp. and the like).

Fleas are a particular problem because not only do they adversely affect the health of the animal or human, but they also cause a great deal of psychological stress. Moreover, fleas are also vectors of pathogenic agents in animals, such as dog tapeworm (*Dipylidium caninum*), and humans.

Similarly, ticks are also harmful to the physical and psychological health of the animal or human. However, the most serious problem associated with ticks is that they are the vector of pathogenic agents in both humans and animals. Major diseases which are caused by ticks include borrelioses (Lyme disease caused by *Borrelia burgdorferi*), babesioses (or piroplasmoses caused by *Babesia* spp.) and rickettsioses (also known as Rocky Mountain spotted fever). Ticks also release toxins which cause inflammation or paralysis in the host. Occasionally, these toxins are fatal to the host.

Moreover, mites and lice are particularly difficult to combat since there are very few active substances which act on these parasites and they require frequent treatment.

Likewise, farm animals are also susceptible to parasite infestations. For example, cattle are affected by a large number of parasites. A parasite which is very prevalent among farm animals is the tick genus *Boophilus*, especially those of the species *microplus* (cattle tick), *decoloratus* and *annulatus*. Ticks, such as *Boophilus microplus*, are particularly difficult to control because they live in the pasture where farm animals graze. Other important parasites of cattle and sheep are listed as follows:

myiases-causing flies such as *Dermatobia hominis* (known as Berne in Brazil) and *Cochlyomia hominivorax* (greenbottle); sheep myiases-causing flies such as *Lucilia sericata, Lucilia cuprina* (known as blowfly strike in Australia, New Zealand and South Africa). These are flies whose larva constitutes the animal parasite;

flies proper, namely those whose adult constitutes the parasite, such as *Haematobia irritans* (horn fly);

lice such as *Linognathus vitulorum*, etc.; and mites such as *Sarcoptes scabiei* and *Psoroptes ovis*.

1-arylpyrazoles as a class of chemicals are well known in the art, and certain compounds in this class have been found to be potently active against a wide range of pests and parasites that are harmful to animals and plants. For example, 1-arylpyrazole derivatives are known in the art to prevent, treat or control ectoparasitic infestations in mammals, such as cats, dogs and cattle. Certain 1-arylpyrazoles and their use against pests are described in U.S. Pat. Nos. 4,963,575; 5,122,530; 5,232,940; 5,236,938; 5,246,255; 5,547,974; 5,567,429; 5,576,429; 5,608,077; 5,714,191; 5,814,652; 5,885,607; 5,567,429; 5,817,688; 5,885,607; 5,916,618; 5,922,885; 5,994,386; 6,001,384; 6,010,710; 6,057,355; 6,069,157; 6,083,519; 6,090,751; 6,096,329; 6,124,339; 6,180,798; 6,335,357; 6,350,771; 6,372,774; 6,395,906; 6,413,542; 6,685,954; and 7,468,381, 7,514,561, 7,517,877, 7,759,381 and 7,834,003. See also: EP 0 234 119, EP 0 295 117, EP 0 352 944, EP 0 500 209, EP 0 780 378, EP 0 846 686, and EP 0 948 485, all of which are incorporated herein by reference in their entirety.

The compounds of the families defined in these patents are extremely active and one of these compounds, 5-amino-3-cyano-1-(2,6-dichloro-4-trifluoromethylphenyl)-4-trifluoromethylsulfinylpyrazole, or fipronil, is particularly effective against pests, including fleas and ticks.

U.S. Pat. No. 7,759,381 describes certain 1-arylpyrazole compounds that are substituted at the 5-position of the pyrazole ring with alkyl or $C_1$-$C_4$ haloalkyl groups. These compounds were also found to be particularly effective against fleas and ticks.

These compounds are given as having activity against a very large number of parasites, including insects and acarines in fields as varied as agriculture, public health and veterinary medicine. The general teaching of these documents indicates that these active compounds may be administered via different routes: oral, parenteral, percutaneous and topical routes. Topical administration comprises, in particular, skin solutions (pour-on or spot-on), sprays, drenches, baths, showers, jets, powders, greases, shampoos, creams, etc. The pour-on type skin solutions may be designed for percutaneous administration.

Notwithstanding the effectiveness of certain arylpyrazole compounds on certain parasites, there continues to be a need for new formulations comprising 1-arylpyrazoles in pharmaceutically acceptable carriers that exhibit improved efficacy against parasites.

Other compounds that are known in the art to prevent, treat or control endo- and ectoparasitic infestations include milbemycin or avermectin derivatives, which are natural or semi-synthetic compounds that contain a 16-membered macrocyclic ring. The avermectin and milbemycin series of compounds are potent anthelmintic and antiparasitic agents against a wide range of internal and external parasites. The natural product avermectins are disclosed in U.S. Pat. No. 4,310,519 to Albers-Schonberg, et al., and the 22,23-dihydro-avermectin compounds are disclosed in Chabala, et al., U.S. Pat. No. 4,199,569. For a general discussion of avermectins, which include a discussion of their uses in humans and animals, see "Ivermectin and Abamectin," W. C. Campbell, ed., Springer-Verlag, New York (1989). Naturally occurring milbemycins are described in Aoki et al., U.S. Pat. No. 3,950,360.

Another family of parasiticides are the formamidines which include but are not limited to amitraz (MITABAN®, Pfizer; POINT-GUARD®, Intervet; PREVENTIC®, Virbac; TAKTIC®, Intervet), chlordimeform, chloromebuform, formetanate and formparanate. Amitraz is a well-known acaracide/insecticide from the formamidine family acknowledged to be useful as a miticidal agent and for the control of ticks. See *Plumb's Veterinary Drug Handbook* (*Fifth Edition*), ed. Donald C. Plumb, Blackwell Publishing, pg. 34, (2005). The formamidine family of compounds is distinguished by a characteristic —N=CR—NR'-moiety. Amitraz differs from other members of the formamidine family in that there are two such moieties in the molecule. Amitraz has the following structure:

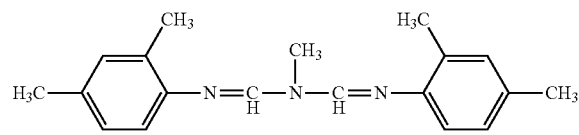

One problem associated with compositions comprising formamidine compounds, including amitraz, is the lack of long-term stability under certain conditions. For example, amitraz has been shown to degrade in aqueous solutions at certain pH ranges, as described, for example, in E. Corta, A. Bakkali, L. A. Berrueta, B. Gallo, F. Vicente, "Kinetics and Mechanism of Amitraz Hydrolysis in Aqueous Media by HPLC and GC-MS", Talanta 48 (1999) 189-199. Some amitraz degradates have further shown pesticidal efficacy, such as described, for example, in Osborne, M. P., "Actions of Formamidines, Local Anesthetics, Octopamine and Related Compounds Upon the Electrical Activity of Neurohaemal Organs of the Stick Insect (*Carausius morosus*) and Sense Organs of Fly Larvae (*Musca demstica, Calliphora erythrocephala*)", Pesticide Biochemistry and Physiology 23, 190-204 (1985).

Therefore, although formamidine parasiticides, including amitraz, have considerable utility for treating and preventing parasitic infestations, there are several problems associated with using amitraz as a parasiticide in a commercial veterinary pharmaceutical product. These problems include: (1) insufficient stability at certain pH values: while amitraz is stable at higher pH values, amitraz tends to hydrolyze over time at pH ranges commonly associated with physiological use (e.g., pH of about 5.0 to about 6.0); (2) amitraz is not effective for the control of fleas; and (3) compositions comprising amitraz may not provide a sufficiently long term shelf life in mixtures with some antiparisitic agents and certain carriers. For example, compositions containing amitraz may not have sufficient long term stability (shelf life) in certain solvent systems which are optimal for other antiparasitic agents with which it may be combined.

A composition comprising a 1-aryl-pyrazole with a formamidine compound, e.g. fipronil with amitraz, which exhibits synergistic efficacy against ectoparasites is described in U.S. Pat. No. 7,531,186 to Boeckh et al.; however certain embodiments of the composition, where a 1-arylpyrazole and a formamidine are present together in certain carriers, may not have a sufficiently long storage shelf life. One possible reason for the insufficient long term shelf life is that fipronil is stable at a pH of about 5.0 to about 6.0, while amitraz will degrade at this pH range.

Interestingly, another family of compounds generally known as substituted imidazoles has been shown to have modest insecticidal activity. This class of compounds is also known for activity at alpha-1 and alpha-2 adrenergic receptors. See, e.g., Whitlock et al., Bioorganic & Medicinal Chemistry Letters, 18, (2008), 2930-2934 and Whitlock et al., Bioorganic & Medicinal Chemistry Letters, 19, (2009), 3118-3121 regarding partial agonist activity of substituted imidazoles at alpha-1A adrenoceptors.

U.S. Pat. No. 7,417,057 and its divisional U.S. Pat. No. 7,767,667 to Dixson et al., disclose pesticidal heterocycles that include imidazole derivatives. The pesticidal heterocycles of the '057 and '667 patents were demonstrated to be moderately active against cotton aphids at high concentration (300 ppm for 24 hours).

U.S. Pat. No. 7,592,362 and its divisional U.S. Pat. No. 7,825,149 to Chubb et al., disclose hundreds of imidazole compounds that are reportedly useful as paraciticides although no data in the patents show this.

WO 2010/020896 to Chubb et al., discloses a combination of an alpha substituted 2-benzyl substituted imidazole, a 1-arylpyrazole (e.g., fipronil), and optionally an insect growth regulator (e.g., s-methoprene). Tested in vivo formulations demonstrated some efficacy against *C. felis* (i.e., cat fleas) out to 35 days and against *I. ricinus* (i.e., castor bean tick) out to day 28.

WO 2011/092604 to Chubb et al., discloses a combination of demiditraz, fipronil, an acid modifier, and optionally at least one antioxidant.

Despite the work done to date synthesizing compounds to control parasites, there remains a need in the art for formulations, methods of storage and methods of administration for animal parasiticides in a synergistically active formulation.

Citation or identification of any document in this application is not an admission that such document is available as prior art to the present invention.

SUMMARY OF THE INVENTION

The present invention provides compositions and formulations comprising a 1-arylpyrazole compound in combination with a substituted imidazole compound, formulations and uses or veterinary uses thereof for the treatment or prophylaxis of parasitic infestations of animals (either wild or domesticated), including livestock and companion animals such as cats, dogs, horses, chickens, sheep, goats, pigs, turkeys and cattle, with the aim of ridding these hosts of parasites commonly encountered by such animals.

The invention also provides methods for the treatment or prevention of parasitic infestations in animals, comprising administering an effective amount of a 1-arylpyrazole in combination with at least one substituted imidazole compound to the animal. Surprisingly, it has been found that the inventive compositions and formulations described herein exhibit superior stability and synergistic efficacy against harmful parasites over a long duration compared with compositions known in the art. In particular, the present invention has surprisingly overcome the problems associated with the instability of a formamidine in solution and the problems associated with the instability of a solution comprising a 1-arylpyrazole and a formamidine.

The compositions or formulations of the invention include spot-on, pour-on or spray formulations and may include a further ectoparasiticide, such as an insect growth regulator (IGR), an avermectin or milbemycin derivative, an acaricide, a pyrethroid insecticide, or an anthelmintic, such as benzimidazoles or imidazothiazoles.

One aspect of the invention provides compositions comprising at lest one 1-aryl-5-alkyl or 1-aryl-5-haloakylpyrazole compound of formula (IA)

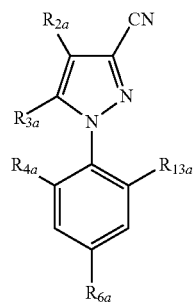

(IA)

wherein variables $R_{2a}$, $R_{3a}$, $R_{4a}$, $R_{6a}$ and $R_{13a}$ are as defined below, in combination with a substituted imidazole hereafter defined, a veterinarily acceptable carrier, and optionally with at least one crystallization inhibitor.

In some embodiments, the 1-arylpyrazole compounds have the formula (IB) shown below, where the variables $R_{2b}$, $R_{3b}$, $R_{4b}$, $R_{6b}$ and Z are described below.

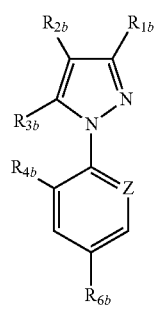

(IB)

In other embodiments, the substituted imidazole compounds in the compositions of the invention have the formula (II) shown below, where variables $X_1$, $X_2$, $X_3$, $X_4$, $X_5$, $X_6$, $X_7$ and $X_8$ are described below.

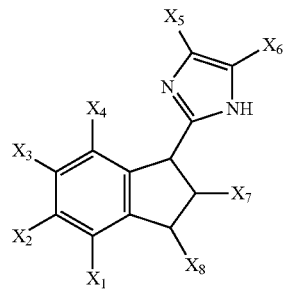

(II)

In yet other embodiments, the substituted imidazole compounds in the compositions of the invention have the formula (III) shown below, where variables $X_1$, $X_2$, $X_3$, $X_4$, $X_5$, $X_6$, $X_7$ and $X_8$ are described below.

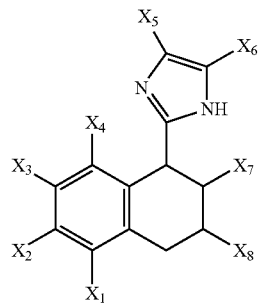

(III)

In some embodiments, the invention provides compositions and methods comprising at least one 1-arylpyrazole compound and at least one substituted imidazole compound in a veterinarily acceptable carrier. The methods and compositions allow for stable synergistic compositions comprising 1-arylpyrazole compounds and substituted imidazole compounds that have superior activity against parasites. In some embodiments, the 1-arylpyrazole compound is fipronil and the substituted imidazole compound is 1H-imidazole, 2-(2,3-dihydro-7-methyl-1H-inden-1-yl). In some embodiments, the 1-arylpyrazole compound(s) is administered simultaneously with the substituted imidazole compound(s) in a common carrier.

Also provided are stable 1-arylpyrazole and substituted imidazole combination compositions in certain carriers. In some embodiments, the carriers include solvents with dielectric constants of about 2 to about 30 that are acceptable for pharmaceutical or veterinary use. In other embodiments, the carriers include aprotic solvents or polar aprotic solvents. In still other embodiments, the carrier includes aprotic solvents or polar aprotic solvents with dielectric constants of about 2 to about 30.

The invention also provides a kit for the treatment or prevention of a parasitic infestation in an animal, which comprises at least one 1-arylpyrazole compound in combination with at least one substituted imidazole compound in a common veterinarily acceptable carrier, and a container.

Accordingly, it is an object of the invention to not encompass within the invention any previously known product, process of making the product, or method of using the product such that the Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

These and other embodiments are disclosed or are obvious from and encompassed by, the following Detailed Description.

DETAILED DESCRIPTION

The present invention provides novel and inventive compositions and formulations comprising at least one 1-arylpyrazole compound in combination with one or more substituted imidazole compound(s) and a veterinarily acceptable carrier or diluent. Also provided are methods and uses for the treatment or prophylaxis of parasitic infections and infestations of animals, comprising administering an effective amount of a composition of the invention to the animal. Surprisingly, it has been found that the inventive compositions and formulations described herein comprising a 1-arylpyrazole compound in combination with a substituted imidazole compound exhibits superior stability and efficacy, including synergistic efficacy in some embodiments, against harmful parasites. In particular, the present invention has surprisingly overcome the problems associated with other formulations, such as the lack of long term stability of a formamidine in solution and the problems associated with the insufficient shelf life of a composition comprising a 1-arylpyrazole and a formamidine in certain carriers.

The invention includes at least the following features:

(a) In one embodiment, the invention provides novel veterinary compositions comprising at least one 1-arylpyrazole of formula (I), or veterinarily acceptable salts thereof, together with a substituted imidazole of formula (II) or formula (III) and a veterinarily acceptable carrier or diluent, that exhibit superior activity against animal parasites and improved stability;

(b) methods for the treatment or prevention of parasitic infestations in an animal comprising administering an effective amount of a composition comprising at least one 1-arylpyrazole of formula (I), or veterinarily acceptable salts thereof, and a substituted imidazole of formula (II) or formula (III), or veterinarily acceptable salts thereof, to the animal in a veterinarily acceptable carrier or diluent;

(c) methods for the treatment or prevention of parasitic infestations in animals comprising administering an effective amount of at least one 1-arylpyrazole of formula (I) and at least one substituted imidazole of formula (II) or formula (III), or veterinarily acceptable salts thereof, together with veterinarily acceptable carriers or diluents, wherein the 1-arylpyrazole(s) and the substituted imidazole compound(s) are administered simultaneously;

(d) methods for the treatment or prevention of parasitic infestations in animals comprising administering an effective amount of at least one 1-arylpyrazole of formula (I) and at least one substituted imidazole of formula (II) or formula (III), or veterinarily acceptable salts thereof, together with veterinarily acceptable carriers or diluents, wherein the 1-arylpyrazole(s) and the substituted imidazole(s) are administered simultaneously and the 1-arylpyrazole(s) and the substituted imidazole(s) are in separate carriers;

(e) methods for the treatment or prevention of parasitic infestations in animals comprising administering an effective amount of at least one 1-arylpyrazole of formula (I) and at least one substituted imidazole of formula (II) or formula (III), or veterinarily acceptable salts thereof, together with veterinarily acceptable carriers or diluents, wherein 1-arylpyrazole(s) and the substituted imidazole(s) are administered simultaneously using a container that holds the 1-arylpyrazole and the substituted imidazole in a common carrier.

In this disclosure and in the claims, terms such as "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

It is also noted that in this disclosure and in the claims or paragraphs, the compounds of the invention are intended to include all stereoisomers and crystalline forms (which includes hydrated forms, polymorphic forms and amorphous forms with up to 15% by weight crystalline structure) thereof.

Definitions

Terms used herein will have their customary meaning in the art unless specified otherwise. The organic moieties mentioned in the definitions of the variables of formula (I) or (II) are—like the term halogen—collective terms for individual listings of the individual group members. The prefix $C_n$-$C_m$ indicates in each case the possible number of carbon atoms in the group.

The term "animal" is used herein to include all mammals, birds and fish and also include all vertebrate animals, including humans. Animals include, but are not limited to, humans, cats, dogs, cattle, chickens, cows, deer, goats, horses, llamas, pigs, sheep and yaks. It also includes an individual animal in all stages of development, including embryonic and fetal stages.

The term "alkyl" refers to saturated straight, branched, cyclic, primary, secondary or tertiary hydrocarbons, including those having 1 to 20 atoms. In some embodiments, alkyl groups will include $C_1$-$C_{12}$, $C_1$-$C_{10}$, $C_1$-$C_8$, $C_1$-$C_6$ or $C_1$-$C_4$ alkyl groups. Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

Cyclic alkyl groups, which are encompassed by alkyl, may be referred to as "cycloalkyl" and include those with 3 to 10 carbon atoms having single or multiple condensed rings. In some embodiments, cycloalkyl groups include $C_4$-$C_7$ or $C_3$-$C_4$ cyclic alkyl groups. Non-limiting examples of cycloalkyl groups include adamantyl, cyclopropyl, cyclobutyl, cyclopentyl, cyclohexyl, cycloheptyl, cyclooctyl and the like.

The alkyl and cycloalkyl groups described herein can be unsubstituted or substituted with one or more moieties selected from the group consisting of alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamoyl, ester, phosphonyl, phosphinyl, phosphoryl, phosphine, thioester, thioether, acid halide, anhydride, oxime, hydrozine, carbamate, phosphonic acid, phosphate, phosphonate, or any other viable functional group that does not inhibit the biological activity of the compounds of the invention, either unprotected, or protected as necessary, as known to those skilled in the art, for example, as taught in Greene, et al., Protective Groups in Organic Synthesis, John Wiley and Sons, Third Edition, 1999, hereby incorporated by reference.

The term "alkenyl" refers to both straight and branched carbon chains which have at least one carbon-carbon double bond. In some embodiments, alkenyl groups may include $C_2$-$C_{20}$ alkenyl groups. In other embodiments, alkenyl includes $C_2$-$C_{12}$, $C_2$-$C_{10}$, $C_2$-$C_8$, $C_2$-$C_6$ or $C_2$-$C_4$ alkenyl groups. In one embodiment of alkenyl, the number of double bonds is 1-3, in another embodiment of alkenyl, the number of double bonds is one or two. Other ranges of carbon-carbon double bonds and carbon numbers are also contemplated depending on the location of the alkenyl moiety on the molecule. "$C_2$-$C_{10}$-alkenyl" groups may include more than one double bond in the chain. Examples include, but are not limited to, ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

"Cycloalkenyl" refers to monovalent cyclic alkenyl groups of from 4 to 10 carbon atoms, preferably 5 to 8 carbon atoms, having single or multiple condensed rings which condensed rings may or may not be cycloalkenyl provided that the point of attachment is to a cycloalkenyl ring atom. Examples of cycloalkenyl groups include, by way of example, cyclopenten-4-yl, cyclooctene-5-yl and the like. Alkenyl and cycloalkenyl groups may be unsubstituted or substituted with one or more substituents as described for alkyl above.

"Alkynyl" refers to both straight and branched carbon chains which have at least one carbon-carbon triple bond. In one embodiment of alkynyl, the number of triple bonds is 1-3; in another embodiment of alkynyl, the number of triple bonds is one or two. In some embodiments, alkynyl groups include from $C_2$-$C_{20}$ alkynyl groups. In other embodiments, alkynyl groups may include $C_2$-$C_{12}$, $C_2$-$C_{10}$, $C_2$-$C_8$, $C_2$-$C_6$ or $C_2$-$C_4$ alkynyl groups. Other ranges of carbon-carbon triple bonds and carbon numbers are also contemplated depending on the location of the alkenyl moiety on the molecule. For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

The term "haloalkyl" refers to an alkyl group, as defined herein, which is substituted by one or more halogen atoms. For example $C_1$-$C_4$-haloalkyl includes, but is not limited to, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like.

The term "fluoroalkyl" as used herein refers to an alkyl in which one or more of the hydrogen atoms is replaced with fluorine atoms, for example difluoromethyl, trifluoromethyl, 1-fluoroethyl, 2-fluoroethyl, 2,2-difluoroethyl, 2,2,2-trifluoroethyl, 1,1,2,2-tetrafluoroethyl or pentafluoroethyl.

The term "haloalkenyl" refers to an alkenyl group, as defined herein, which is substituted by one or more halogen atoms.

The term "haloalkynyl" refers to an alkynyl group, as defined herein, which is substituted by one or more halogen atoms.

"Alkoxy" refers to alkyl-O—, wherein alkyl is as defined above. Similarly, the terms "alkenyloxy," "alkynyloxy," "haloalkoxy," "haloalkenyloxy," "haloalkynyloxy," "cycloalkoxy," "cycloalkenyloxy," "halocycloalkoxy," and "halocycloalkenyloxy" refer to the groups alkenyl-O—, alkynyl-O—, haloalkyl-O—, haloalkenyl-O—, haloalkynyl-O—, cycloalkyl-O—, cycloalkenyl-O—, halocycloalkyl-O—, and halocycloalkenyl-O—, respectively, wherein alkenyl, alkynyl, haloalkyl, haloalkenyl, haloalkynyl, cycloalkyl, cycloalkenyl, halocycloalkyl, and halocycloalkenyl are as defined above. Examples of $C_1$-$C_6$-alkoxy include, but are not limited to, methoxy, ethoxy, $C_2H_5$—$CH_2O$—, $(CH_3)_2CHO$—, n-butoxy, $C_2H_5$—$CH(CH_3)O$—, $(CH_3)_2CH$—$CH_2O$—, $(CH_3)_3CO$—, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy and the like.

"Aryl" refers to a monovalent aromatic carbocyclic group of from 6 to 14 carbon atoms having a single ring or multiple condensed rings. In some embodiments, aryl groups include $C_6$-$C_{10}$ aryl groups. Aryl groups include, but are not limited to, phenyl, biphenyl, naphthyl, tetrahydronaphtyl, phenylcyclopropyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, cycloalkylthio, halocycloalkylthio, alkylsulfinyl, alkenylsulfinyl, alkynyl-sulfinyl, haloalkylsulfinyl, haloalkenylsulfinyl, haloalkynylsulfinyl, alkylsulfonyl, alkenylsulfonyl, alkynylsulfonyl, haloalkyl-sulfonyl, haloalkenylsulfonyl, haloalkynylsulfonyl, alkylamino, alkenylamino, alkynylamino, di(alkyl)amino, di(alkenyl)-amino, di(alkynyl)amino, or trialkylsilyl.

The term "aralkyl" refers to an aryl group that is bonded to the parent compound through a diradical alkylene bridge, (—$CH_2$—)$_n$, where n is 1-12 and where "aryl" is as defined above.

"Heteroaryl" refers to a monovalent aromatic group of from 1 to 15 carbon atoms, preferably from 1 to 10 carbon atoms, having one or more oxygen, nitrogen, and sulfur heteroatoms within the ring, preferably 1 to 4 heteroatoms, or 1 to 3 heteroatoms. The nitrogen and sulfur heteroatoms may optionally be oxidized. Such heteroaryl groups can have a single ring (e.g., pyridyl or furyl) or multiple condensed rings provided that the point of attachment is through a heteroaryl ring atom. Preferred heteroaryls include pyridyl, piridazinyl, pyrimidinyl, pyrazinyl, triazinyl, pyrrolyl, indolyl, quinolinyl, isoquinolinyl, quinazolinyl, quinoxalinnyl, furanyl, thiophenyl, furyl, pyrrolyl, imidazolyl, oxazolyl, isoxazolyl, isothiazolyl, pyrazolyl benzofuranyl, and benzothiophenyl. Heteroaryl rings may be unsubstituted or substituted by one or more moieties as described for aryl above.

"Heterocyclyl," "heterocyclic" or "heterocyclo" refers to fully saturated or unsaturated, cyclic groups, for example, 3 to 7 membered monocyclic or 4 to 7 membered monocyclic; 7 to 11 membered bicyclic, or 10 to 15 membered tricyclic ring systems, which have one or more oxygen, sulfur or nitrogen heteroatoms in ring, preferably 1 to 4 or 1 to 3 heteroatoms. The nitrogen and sulfur heteroatoms may optionally be oxidized and the nitrogen heteroatoms may optionally be quaternized. The heterocyclic group may be attached at any heteroatom or carbon atom of the ring or ring system and may be unsubstituted or substituted by one or more moieties as described for aryl groups above.

Exemplary monocyclic heterocyclic groups include, but are not limited to, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

Exemplary bicyclic heterocyclic groups include, but are not limited to, indolyl, benzothiazolyl, benzoxazolyl, benzodioxolyl, benzothienyl, quinuclidinyl, quinolinyl, tetra-hydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3, 2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include carbazolyl, benzidolyl, phenanthrolinyl, acridinyl, phenanthridinyl, xanthenyl, and the like.

Alkoxycarbonyl refers to —C(=O)—O-alkyl, wherein alkoxy is as defined above;

Halogen means the atoms fluorine, chlorine, bromine and iodine. The designation of "halo" (e.g. as illustrated in the term haloalkyl) refers to all degrees of substitutions from a single substitution to a perhalo substitution (e.g. as illustrated with methyl as chloromethyl (—$CH_2Cl$), dichloromethyl (—$CHCl_2$), trichloromethyl (—$CCl_3$)).

Stereoisomers and Polymorphic Forms

It will be appreciated by those of skill in the art that the compounds within the compositions of the invention may exist and be isolated as optically active and racemic forms. Compounds having one or more chiral centers, including at a sulfur atom, may be present as single enantiomers or diastereomers or as mixtures of enantiomers or diastereomers. For example, it is well known in the art that sulfoxide compounds may be optically active and may exist as single enantiomers or racemic mixtures. In addition, compounds within the compositions of the invention may include one or more chiral centers, which results in a theoretical number of optically active isomers. Where compounds within the compositions of the invention include n chiral centers, the compounds may comprise up to $2^n$ optical isomers. The present invention encompasses the specific enantiomers or diastereomers of each compound as well as mixtures of different enantiomers or diastereomers of the compounds of the invention that possess the useful properties described herein. The optically active forms can be prepared by, for example, resolution of the racemic forms by selective crystallization techniques, by synthesis from optically active precursors, by chiral synthesis, by chromatographic separation using a chiral stationary phase or by enzymatic resolution.

The compounds within the compositions of present invention may also be present in different solid forms such as different crystalline forms or in the form of an amorphous solid. The present invention encompasses different crystalline forms as well as amorphous forms of the inventive compounds.

In addition, the compounds within the compositions of the invention may exist as hydrates or solvates, in which a certain stoichiometric amount of water or a solvent is associated with the molecule in the crystalline form. The hydrates and solvates of the compounds of formula (I), (II) and (III) are also the subject of the invention.

Salts

Also contemplated within the scope of the invention are acid or base salts, where applicable, of the compounds of the invention provided for herein.

The term "acid" contemplates all pharmaceutically acceptable inorganic or organic acids. Inorganic acids include mineral acids such as hydrohalic acids such as hydrobromic acid and hydrochloric acid, sulfuric acid, phosphoric acids and nitric acid. Organic acids include all pharmaceutically acceptable aliphatic, alicyclic and aromatic carboxylic acids, dicarboxylic acids, tricarboxylic acids and fatty acids. In one embodiment of the acids, the acids are straight chain or branched, saturated or unsaturated $C_1$-$C_{20}$ aliphatic carboxylic acids, which are optionally substituted by halogen or by hydroxyl groups, or $C_6$-$C_{12}$ aromatic carboxylic acids. Examples of such acids are carbonic acid, formic acid, acetic acid, propionic acid, isopropionic acid, valeric acid, α-hydroxy acids such as glycolic acid and lactic acid, chloroacetic acid, benzoic acid, methane sulfonic acid, and salicylic acid. Examples of dicarboxylic acids include oxalic acid, malic acid, succinic acid, tartaric acid, fumaric acid, and maleic acid. An example of a tricarboxylic acid is citric acid. Fatty acids include all pharmaceutically or veterinarily acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

The term "base" contemplates all pharmaceutically or veterinarily acceptable inorganic or organic bases, including hydroxides, carbonates or bicarbonates of alkali metal or alkaline earth metals. Salts formed with such bases include, for example, the alkali metal and alkaline earth metal salts, including, but not limited to, as the lithium, sodium, potassium, magnesium or calcium salts. Salts formed with organic bases include the common hydrocarbon and heterocyclic amine salts, which include, for example, ammonium salts ($NH_4^+$), alkyl- and dialkylammonium salts, and salts of cyclic amines such as the morpholine and piperidine salts.

One aspect of the invention provides a formulation with increased stability or efficacy for treating or preventing an infestation of an animal with ectoparasites or endoparasites comprising:

a veterinary formulation comprising:

(a) a 1-aryl-5-alkyl or 5-haloalkylpyrazole of formula (IA) or a veterinarily acceptable salt thereof,

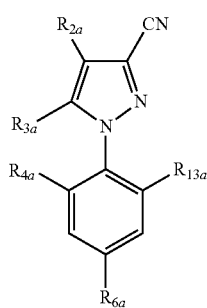

(IA)

wherein:
$R_{2a}$ is —S(O)$_m$R$_{11a}$;
$R_{3a}$ is methyl, ethyl or $C_1$-$C_4$ haloalkyl;
$R_{4a}$ is halogen;
$R_{6a}$ is $C_1$-$C_4$ alkyl or haloalkyl;
$R_{13a}$ is halogen;
$R_{11a}$ is $C_1$-$C_4$ haloalkyl; and
m is 0, 1 or 2;

(b) at least one substituted imidazole compound of the general formula (II) or a veterinarily acceptable salt thereof:

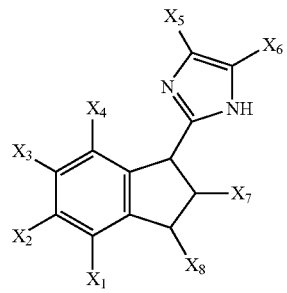

(II)

where
$X_1$ is H, halogen or $CH_3$;
$X_2$ is H;
$X_3$ is H, $CH_3$, halogen, methoxy, amino, alkenyl, alkynyl or ethyl;
$X_4$ is H or $CH_3$;
$X_5$ is H or $CH_3$;
$X_6$ is H or $CH_3$;
$X_7$ is H or $CH_3$; and
$X_8$ is H;

(c) a veterinarily acceptable carrier; and
(d) optionally a crystallization inhibitor.

Compounds of formula (I) and methods for preparing the compounds are described, for example, in U.S. Pat. Nos. 6,096,329; 6,395,765; 6,685,954; 6,867,229; EP 0 205 117 and WO 87/03781, all of which are incorporated herein by reference in their entirety.

It is another aspect of the invention to provide for formulations comprising 1-arylpyrazole compounds that exhibit improved efficacy and/or stability. It has surprisingly been discovered that spot-on, pour-on or spray-on formulations of 1-arylpyrazole compounds in certain carriers exhibit enhanced stability and/or efficacy against ectoparasites or endoparasites compared to formulations of 1-arylpyrazoles of the prior art.

In one embodiment, the pharmaceutically or veterinarily acceptable carrier comprises acetone, acetonitrile, benzyl alcohol, ethanol, isopropanol, diisobutyl adipate, diisopropyl adipate (also known as CERAPHYL 230), butyl diglycol, dipropylene glycol n-butyl ether, ethylene glycol monoethyl ether, ethylene glycol monomethyl ether, dipropylene glycol monomethyl ether, liquid polyoxyethylene glycols, propylene glycol monomethyl ether, propylene glycol monoethyl ether, 2-pyrrolidone including N-methylpyrrolidone, diethylene glycol monoethyl ether, triacetin, butyl acetate, octyl acetate, propylene carbonate, butylene carbonate, dimethyl sulfoxide, amides including dimethylformamide and dimethylacetamide, or any combination thereof.

In one embodiment of the invention, the pharmaceutically or veterinarily acceptable carrier of the formulation includes $C_1$-$C_{10}$ alcohols or esters thereof (including acetates, such as ethyl acetate, butyl acetate and the like), $C_{10}$-$C_{18}$ saturated fatty acids or esters thereof, $C_{10}$-$C_{18}$ monounsaturated fatty acids or esters thereof, monoesters or diesters of aliphatic diacids, glycerol monoesters (e.g. monoglycerides), glycerol diesters (e.g. diglycerides), glycerol triesters (e.g. triglycerides such as triacetin), glycols, glycol ethers, glycol esters or glycol carbonates, polyethylene glycols of various grades (PEGs) or monoethers, diethers, monoesters or diesters thereof (e.g. diethylene glycol monoethyl ether), or mixtures thereof.

In another embodiment of the invention, the carrier may include diisopropyl adipate, dipropylene glycol monomethyl ether, propylene glycol monomethyl ether, 2-pyrrolidone including N-methylpyrrolidone, diethylene glycol monoethyl ether, triacetin, butyl acetate, octyl acetate, propylene carbonate, oleic acid, or a mixture of at least two of these solvents.

In yet another embodiment of the invention, the carrier may include triacetin or diethylene glycol monoethyl ether.

It is a further aspect of the invention to provide for formulations with enhanced efficacy against ectoparasites, such as fleas, ticks, mites, mosquitoes, flies and lice. The invention may also be effective against endoparasites, cestodes, nematodes, such as filariae, and roundworms of the digestive tract of animals and humans.

In another embodiment of the invention, the pharmaceutically or veterinarily acceptable carrier is an organic solvent commonly used in the formulation art. These organic solvents may be found, for example, in Remington Pharmaceutical Sciences, 16$^{th}$ Edition (1986). These solvents include, for example, acetone, ethyl acetate, methanol, ethanol, isopropanol, dimethylformamide, dichloromethane or diethylene glycol monoethyl ether (TRANSCUTOL), diisobutyl adipate, diisopropyl adipate (CERAPHYL 230), butyl diglycol, dipropylene glycol n-butyl ether, ethylene glycol monoethyl ether, ethylene glycol monomethyl ether, dipropylene glycol monomethyl ether, liquid polyoxyethylene glycols, propylene glycol monomethyl ether, propylene glycol monoethyl ether, 2-pyrrolidone including N-methylpyrrolidone, diethylene glycol monoethyl ether, triacetin, acetates of $C_1$-$C_{10}$ alcohols, $C_{10}$-$C_{18}$ monounsaturated fatty acids or esters thereof, propylene carbonate, butylene carbonate, or any combination thereof. These solvents can be supplemented by various excipients according to the nature of the desired phases, such as $C_8$-$C_{10}$ caprylic/capric triglyceride (ESTASAN or MIGLYOL 812), oleic acid or propylene glycol.

It is herein presented that 1-aryl-5-alkyl or 5-haloalkyl pyrazole compounds are highly efficacious against ectoparasites and provide long-lasting protection against ectoparasites for at least 30, at least 40 or at least 60 days. Thus, 1-aryl-5-alkyl or 5-haloalkyl pyrazoles of formula (IA) are extremely useful and offer substantial advantages to other paraciticidal compounds. Furthermore, it has been discovered that 1-aryl-5-alkyl or 5-haloalkyl pyrazole compounds of formula (IA) are able to eradicate parasites, particularly fleas and ticks, from animals more quickly than other parasiticides.

Compounds of formula (I) and methods for preparing the compounds are described, for example, in U.S. Pat. Nos. 6,096,329; 6,395,765; 6,685,954; 6,867,229; EP 0 205 117 and WO 87/03781, all of which are incorporated herein by reference in their entirety.

It is an aspect of the invention to provide for formulations comprising 1-arylpyrazole compounds that exhibit improved efficacy or stability. It has surprisingly been discovered that spot-on, pour-on or spray-on formulations of 1-arylpyrazole compounds in certain carriers exhibit enhanced stability or efficacy against ectoparasites or endoparasites compared to formulations of 1-arylpyrazoles of the prior art.

In one embodiment, the pharmaceutically or veterinarily acceptable carrier comprises acetone, acetonitrile, benzyl alcohol, ethanol, isopropanol, diisobutyl adipate, diisopropyl adipate (also known as CERAPHYL 230), butyl diglycol, dipropylene glycol n-butyl ether, ethylene glycol monoethyl ether, ethylene glycol monomethyl ether, dipropylene glycol monomethyl ether, liquid polyoxyethylene glycols, propylene glycol monomethyl ether, propylene glycol monoethyl ether, 2-pyrrolidone including N-methylpyrrolidone, diethylene glycol monoethyl ether, triacetin, butyl acetate, octyl acetate, propylene carbonate, butylene carbonate, dimethyl sulfoxide, amides including dimethylformamide and dimethylacetamide, or any combination thereof.

In one embodiment of the invention, the pharmaceutically or veterinarily acceptable carrier of the formulation includes $C_1$-$C_{10}$ alcohols or esters thereof (including acetates, such as ethyl acetate, butyl acetate and the like), $C_{10}$-$C_{18}$ saturated fatty acids or esters thereof, $C_{10}$-$C_{18}$ monounsaturated fatty acids or esters thereof, monoesters or diesters of aliphatic diacids, glycerol monoesters (e.g. monoglycerides), glycerol diesters (e.g. diglycerides), glycerol triesters (e.g. triglycerides such as triacetin), glycols, glycol ethers, glycol esters or glycol carbonates, polyethylene glycols of various grades (PEGs) or monoethers, diethers, monoesters or diesters thereof (e.g. diethylene glycol monoethyl ether), or mixtures thereof.

In another embodiment of the invention, the carrier may include diisopropyl adipate, dipropylene glycol monomethyl ether, propylene glycol monomethyl ether, 2-pyrrolidone including N-methylpyrrolidone, diethylene glycol monoethyl ether, triacetin, butyl acetate, octyl acetate, propylene carbonate, oleic acid, or a mixture of at least two of these solvents.

In yet another embodiment of the invention, the carrier may include triacetin or diethylene glycol monoethyl ether.

It is a further aspect of the invention to provide for formulations with enhanced efficacy against ectoparasites, such as fleas, ticks, mites, mosquitoes, flies and lice. The invention may also be effective against endoparasites, cestodes, nematodes (such as filariae), and roundworms of the digestive tract of animals and humans.

In another embodiment of the invention, the pharmaceutically or veterinarily acceptable carrier is an organic solvent commonly used in the formulation art. These organic solvents may be found, for example, in Remington Pharmaceutical Sciences, 16$^{th}$ Edition (1986). These solvents include, for example, acetone, ethyl acetate, methanol, ethanol, isopropanol, dimethylformamide, dichloromethane or diethylene glycol monoethyl ether (TRANSCUTOL), diisobutyl adipate, diisopropyl adipate (CERAPHYL 230), butyl diglycol, dipropylene glycol n-butyl ether, ethylene glycol monoethyl ether, ethylene glycol monomethyl ether, dipropylene glycol monomethyl ether, liquid polyoxyethylene glycols, propylene glycol monomethyl ether, propylene glycol monoethyl ether, 2-pyrrolidone including N-methylpyrrolidone, diethylene glycol monoethyl ether, triacetin, acetates of $C_1$-$C_{10}$ alcohols, $C_{10}$-$C_{18}$ monounsaturated fatty acids or esters thereof, propylene carbonate, butylene carbonate, or any combination thereof. These solvents can be supplemented by various excipients according to the nature of the desired phases, such as $C_8$-$C_{10}$ caprylic/capric triglyceride (ESTASAN or MIGLYOL 812), oleic acid or propylene glycol.

Another aspect of the invention provides a composition comprising one or more substituted imidazole compounds of formula (II) or formula (III) that exhibit enhanced stability. Examples of the substituted imidazole of the present invention may be as follows:

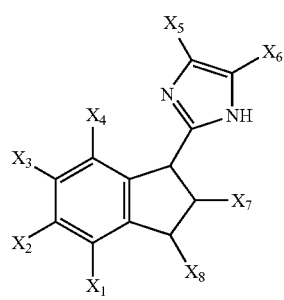

(II)

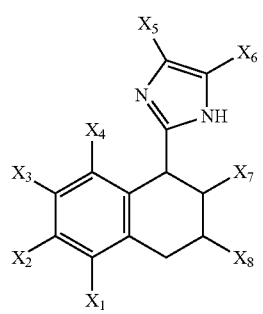

(III)

TABLE 1

Example Compounds of Formula (II)

| Cmpd. No. | X₁ | X₂ | X₃ | X₄ | X₅ | X₆ | X₇ | X₈ |
|---|---|---|---|---|---|---|---|---|
| 1 | H | H | H | H | H | H | H | H |
| 2 | H | H | H | H | H | H | H | H |
| 3 | H | H | F | H | H | H | H | H |
| 4 | H | H | OCH₃ | H | H | H | H | H |
| 5 | H | H | OCH₃ | H | H | H | H | H |
| 6 | H | H | OCH₃ | H | H | H | H | H |
| 7 | H | H | OCH₃ | H | H | H | H | H |
| 8 | Cl | H | H | H | H | H | H | H |
| 9 | H | H | H | H | H | H | H | H |
| 10 | H | H | Cl | H | H | H | H | H |
| 11 | H | H | Cl | H | H | H | H | H |
| 12 | CH₃ | H | H | H | H | H | H | H |
| 13 | H | H | H | H | H | H | H | H |
| 14 | H | H | H | H | H | H | H | H |
| 15 | H | H | H | CH₃ | H | H | H | H |
| 16 | H | H | H | CH₃ | H | H | H | H |
| 17 | H | H | H | H | H | H | H | H |
| 18 | H | H | H | H | H | H | H | H |
| 19 | H | H | OCH₃ | H | H | H | H | H |
| 20 | H | H | OCH₃ | H | H | H | H | H |
| 21 | H | H | I | H | H | H | H | H |
| 22 | H | H | Cl | H | H | H | H | H |
| 23 | Cl | H | H | H | H | H | H | H |
| 24 | H | H | OCHF₂ | H | H | H | H | H |
| 25 | H | H | OCF₃ | H | H | H | H | H |
| 26 | H | H | NH₂ | H | H | H | H | H |
| 27 | H | H | CH=CH₂ | H | H | H | H | H |
| 28 | H | H | CH=CHCH₃ | H | H | H | H | H |
| 29 | H | H | C≡CH | H | H | H | H | H |
| 30 | H | H | C≡CCH₃ | H | H | H | H | H |
| 31 | H | H | OCH₃ | H | H | H | CH₃ | H |
| 32 | H | H | OCH₃ | H | CH₃ | H | H | H |
| 33 | H | H | OCH₃ | H | H | CH₃ | H | H |
| 34 | H | H | OCH₃ | H | CH₃ | CH₃ | H | H |
| 35 | H | H | C₂H₅ | H | H | H | H | H |
| 36 | Cl | H | OCH₃ | H | H | H | H | H |
| 37 | H | H | CH₃ | H | H | H | H | H |
| 38 | H | H | F | H | H | H | H | H |
| 39 | H | H | OCH₃ | H | H | H | H | H |
| 40 | CH₃ | H | OCH₃ | H | H | H | H | H |
| 41 | H | H | H | H | H | H | H | H |

TABLE 2

Example Compounds of Formula (III)

| Cmpd. No. | X₁ | X₂ | X₃ | X₄ | X₅ | X₆ | X₇ | X₈ |
|---|---|---|---|---|---|---|---|---|
| 1 | H | H | H | H | H | H | H | H |
| 2 | H | H | H | H | H | H | H | H |
| 3 | H | H | F | H | H | H | H | H |
| 4 | H | H | OCH₃ | H | H | H | H | H |
| 5 | H | H | OCH₃ | H | H | H | H | H |
| 6 | H | H | OCH₃ | H | H | H | H | H |
| 7 | H | H | OCH₃ | H | H | H | H | H |
| 8 | Cl | H | H | H | H | H | H | H |
| 9 | H | H | H | H | H | H | H | H |
| 10 | H | H | Cl | H | H | H | H | H |
| 11 | H | H | Cl | H | H | H | H | H |
| 12 | CH₃ | H | H | H | H | H | H | H |
| 13 | H | H | H | H | H | H | H | H |
| 14 | H | H | H | H | H | H | H | H |
| 15 | H | H | H | CH₃ | H | H | H | H |
| 16 | H | H | H | CH₃ | H | H | H | H |
| 17 | H | H | H | H | H | H | H | H |
| 18 | H | H | H | H | H | H | H | H |
| 19 | H | H | OCH₃ | H | H | H | H | H |
| 20 | H | H | OCH₃ | H | H | H | H | H |
| 21 | H | H | I | H | H | H | H | H |
| 22 | H | H | Cl | H | H | H | H | H |
| 23 | Cl | H | H | H | H | H | H | H |
| 24 | H | H | OCHF₂ | H | H | H | H | H |
| 25 | H | H | OCF₃ | H | H | H | H | H |
| 26 | H | H | NH₂ | H | H | H | H | H |
| 27 | H | H | CH=CH₂ | H | H | H | H | H |
| 28 | H | H | CH=CHCH₃ | H | H | H | H | H |
| 29 | H | H | C≡CH | H | H | H | H | H |
| 30 | H | H | C≡CCH₃ | H | H | H | H | H |
| 31 | H | H | OCH₃ | H | H | H | CH₃ | H |
| 32 | H | H | OCH₃ | H | CH₃ | H | H | H |
| 33 | H | H | OCH₃ | H | H | CH₃ | H | H |
| 34 | H | H | OCH₃ | H | CH₃ | CH₃ | H | H |
| 35 | H | H | C₂H₅ | H | H | H | H | H |
| 36 | Cl | H | OCH₃ | H | H | H | H | H |
| 37 | H | H | CH₃ | H | H | H | H | H |
| 38 | H | H | F | H | H | H | H | H |
| 39 | H | H | OCH₃ | H | H | H | H | H |
| 40 | CH₃ | H | OCH₃ | H | H | H | H | H |
| 41 | H | H | H | H | H | H | H | H |

In some embodiments, the compositions comprise a veterinarily effective amount of a substituted imidazole in combination with a polar aprotic solvent. Aprotic solvents and polar aprotic solvents are well known in the art, and the invention provides compositions comprising any veterinarily acceptable aprotic or polar aprotic solvent that provides sufficient solubility for the substituted imidazole compound may be used. Polar aprotic solvents include carboxylic acid esters, ketones and aryl ethers.

In other embodiments, the stable substituted imidazole compositions of the invention comprise a veterinarily effective amount of one or more substituted imidazole compounds and solvent with a dielectric constant of about 2 to about 30. In some embodiments, the stable substituted imidazole compositions of the invention comprise aprotic solvents that have a dielectric constant of about 2 to about 30. In still other embodiments, the stable substituted imidazole compositions comprise polar aprotic solvents that have a dielectric constant of about 2 to about 30.

In other embodiments of the invention, the carrier comprises a solvent with a dielectric constant of about 2 to about 40, 2 to about 20, 5 to about 30, or 10 to about 30. The solvent with dielectric constants of about 2 to about 40 is an aprotic solvent or a polar aprotic solvent.

In other embodiments, the carrier comprises one or more solvents with a dielectric constant of about 2 to about 15 or about 3 to about 10. In still another embodiment, the dielectric constant of the one or more solvents is about 3.5 to about 10. In another embodiment, the dielectric constant of the one or more solvents is about 4 to about 6.5.

In other embodiments of the invention, the carrier comprises one or more aprotic solvents with dielectric constants of about 2 to about 40, 2 to about 20, 5 to about 30, or 10 to about 30.

In other embodiments, the carrier comprises one or more aprotic solvents with dielectric constants of about 2 to about 15 or about 3 to about 10. In still another embodiment, the dielectric constant of the one or more aprotic solvents is about 3.5 to about 10. In another embodiment, the dielectric constant of the one or more aprotic solvents is about 4 to about 6.5.

In other embodiments of the invention, the carrier comprises one or more polar aprotic solvents with dielectric constants of about 2 to about 40, 2 to about 20, 5 to about 30, or 10 to about 30.

In other embodiments, the carrier comprises one or more polar aprotic solvents with dielectric constants of about 2 to about 15 or about 3 to about 10. In still another embodiment, the dielectric constant of the one or more polar aprotic solvents is about 3.5 to about 10. In another embodiment, the dielectric constant of the one or more polar aprotic solvents is about 4 to about 6.5.

In one embodiment, the carrier comprises a single solvent with a dielectric constant of about 2 to about 30. In still another embodiment, the carrier comprises a mixture of two or more solvents with a dielectric constant of about 2 to about 30, which may preferably be aprotic or polar aprotic.

In still another embodiment, the carrier comprises a solvent with a dielectric constant of about 2 to about 30 in combination with one or more solvents that do not have a dielectric constant of about 2 to about 30.

As discussed above, it has been found that formamidine compounds, and amitraz in particular, may not have sufficient long term stability in certain solvent systems. For example, in certain solvent systems amitraz may not provide a sufficient shelf life for use as a commercial veterinary pharmaceutical product. Therefore, compositions of substituted imidazoles in carriers that exhibit superior stability are highly desired.

In one embodiment, the invention provides a composition comprising a substituted imidazole in combination with a suitable carrier that is stable for up to about 2 months at about 50° C. It will be appreciated by those of skill in the art that a stable composition comprising a substituted imidazole, as described herein, will show less than about 5% degradation of the substituted imidazole compound at the indicated conditions (temperature and relative humidity) relative to the initial measure of purity or concentration, as tested by a suitable stability-indicating method for a given period of time. Preferably, the stability of a formulation is evaluated by HPLC by measuring the change in concentration of the active in the formulation over time against a reference standard.

In another embodiment, the invention provides a composition comprising a substituted imidazole that is stable for at least about 3 months at about 50° C. In still other embodiments, the invention provides a composition comprising a substituted imidazole that is stable for at least about 4 months, at least about 5 months or at least about 6 months at about 50° C.

In another embodiment, the invention provides a composition comprising a substituted imidazole compound that is stable for at least 3 months at about 40° C. and about 75% relative humidity (RH). In still another embodiment, the composition comprising a substituted imidazole compound will be stable for at least 6 months at about 40° C. and 75% RH. In still another embodiment, the composition comprising a substituted imidazole will be stable for at least 9 months at about 40° C. and 75% RH.

In another embodiment, the invention provides a composition comprising a substituted imidazole that is stable for at least about 12 months at about 25° C. and about 60% RH. In other embodiments, the invention provides a composition comprising a substituted imidazole that is stable for at least about 18 months, about 24 months or about 36 months at about 25° C. and about 60% RH.

In some embodiments, the invention provides stable compositions comprising a substituted imidazole in combination with one or more of amides including dimethylformamide, dimethylacetamide, N-methylpyrrolidone and the like; one or more sulfoxides including dimethyl sulfoxide and the like; and combinations thereof.

In one embodiment, the solvent includes aryl ethers including alkoxybenzene compounds; carboxylic acid esters, including aliphatic and aromatic carboxylic acids such as benzoic acid esters, and compounds with multiple carboxylate groups; aliphatic ketones, saturated aliphatic ketones, cyclic ketones, or mixtures thereof.

In another embodiment, the solvent includes $C_1$-$C_{10}$ carboxylic acid esters, phenyl carboxylic acid esters, carboxylic acid benzyl esters, benzoic acid $C_1$-$C_4$ alkyl esters, $C_1$-$C_6$ saturated aliphatic ketones, and mixtures thereof.

Examples of carboxylic acid esters include, but are not limited to $C_1$-$C_{20}$ alkyl esters of alkanoic acids. In one embodiment, the solvent includes $C_1$-$C_{20}$ alkyl esters of $C_1$-$C_{12}$ alkanoic acids. In other embodiments, the solvent includes $C_1$-$C_{12}$ alkyl esters of $C_1$-$C_{12}$ alkanoic acids, $C_1$-$C_{12}$ alkyl esters of $C_1$-$C_{10}$ alkanoic acids, $C_1$-$C_{12}$ alkyl esters of $C_1$-$C_8$ alkanoic acids, $C_1$-$C_{12}$ alkyl esters of $C_1$-$C_6$ alkanoic acids or $C_1$-$C_{12}$ alkyl esters of $C_1$-$C_4$ alkanoic acids. In various embodiments, the solvent includes $C_1$-$C_{12}$ alkyl esters of formic acid, acetic acid, propionic acid, butanoic acid, pentanoic acid, isobutanoic acid, hexanoic acid, heptanoic acid, octanoic acid, nonanoic acid, decanoic acid, and the like.

Also encompassed by the invention are phenyl and benzyl esters of alkyl carboxylic acids. Other carboxylic acid esters include $C_1$-$C_{20}$ alkyl esters of di-carboxylic and tricarboxylic acids including, but not limited to, malonic acid, succinic acid, glutaric acid, adipic acid, citric acid, and the like.

Aromatic carboxylic acid esters are also contemplated, including $C_1$-$C_{20}$ alkyl esters of aromatic carboxylic acids as well as benzyl esters of aromatic carboxylic acids. Non-limiting examples of aromatic carboxylic acids include, but are not limited to, benzoic acid, phenylacetic acid, salicylic acid, mandelic acid, phthalic acid, cynnamic acid, and the like.

Aliphatic ketones that may be used as solvents for veterinary formulations are well known in the art and include, but are not limited to, acetone, methyl ethyl ketone, methyl isobutyl ketone, methyl isopropyl ketone, 2-butanone, 2-pentanone, 3-pentanone, 2-hexanone, 3-hexanone, and the like.

Aryl ethers that may be used include, but are not limited to, $C_1$-$C_{12}$ alkyl-aryl ethers such as anisole and derivatives of anisole, ethyl phenyl ether (phenetole), propyl phenyl ether, butyl phenyl ether, and the like.

In still another embodiment of the invention, the solvent of the substituted imidazole compositions includes $C_1$-$C_4$-alkoxybenzene, $C_1$-$C_{10}$ carboxylic acid esters, phenyl carboxylic acid esters, carboxylic acid benzyl esters, $C_1$-$C_6$ saturated aliphatic ketones, benzoic acid $C_1$-$C_4$ esters or mixtures thereof.

In other embodiments, the solvent includes methoxybenzene (4.33), butyl acetate (5.0), benzyl acetate (5.0), methyl isobutyl ketone (13.1), ethyl benzoate (6.02), benzyl benzoate (4.8), octyl acetate or mixtures thereof. Dielectric constants are given in parentheses.

In one embodiment, the solvent is a mixture of butyl acetate and anisole or a mixture of butyl acetate and methyl isobutyl ketone.

In another embodiment of the invention, the solvent is octyl acetate. In another embodiment, the carrier comprises a mixture of octyl acetate with another aprotic solvent or with a solvent having a dielectric constant of about 2 to about 30. In one embodiment, the solvent will be a polar aprotic solvent with a dielectric constant of about 2 to about 30. In still another embodiment, the carrier comprises a mixture of octyl acetate with one or more of butyl acetate, methyl isobutyl ketone or anisole.

In one embodiment of the invention, the [weight/volume] % solubility of substituted imidazole at room temperature in the solvent is from about 20% to about 50%. In another embodiment, the [weight/volume] % solubility of substituted imidazole at room temperature is from about 24% to about 46%. In still other embodiments, the [weight/volume] % solubility of substituted imidazole at room temperature in the solvent is from about 10% to about 60%, about 20% to about 60%, or about 10% to about 50%.

Yet another aspect of the invention provides a composition for the treatment or prevention of a parasitic infestation in an animal comprising at least one (i.e. one or more) 1-arylpyrazole compound(s) and at least one substituted imidazole compound(s) in combination with one or more pharmaceutically or veterinarily acceptable carrier(s) and optionally a crystallization inhibitor, wherein the 1-arylpyrazole compound (s) and the substituted imidazole compound (s) are in the same carrier.

In one embodiment of the invention, the composition comprises:

(a) at least one 1-arylpyrazole compound of formula (IB):

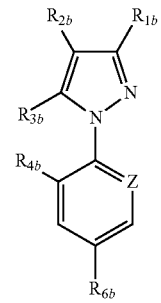

(IB)

in which:

$R_{1b}$ is alkyl, CN or halogen;

$R_{2b}$ is $S(O)_n R_{14b}$ or 4,5-dicyanoimidazol-2-yl or haloalkyl;

$R_{14b}$ is alkyl or haloalkyl;

$R_{3b}$ is a hydrogen, halogen, —$NR_{7b}R_{8b}$, —$S(O)_m R_{9b}$, —$C(O)R_{9b}$, —$C(O)OR_{9b}$, alkyl, haloalkyl, —$OR_{10b}$ or an —N═$C(R_{11b})(R_{12b})$;

$R_{6b}$ is a halogen, haloalkyl, haloalkoxy, $S(O)_q CF_3$ or $SF_5$ group;

$R_{7B}$ and $R_{8B}$ independently represent a hydrogen, alkyl, haloalkyl, —C(O)alkyl, —$S(O)_r CF_3$, acyl or alkoxycarbonyl; or $R_{7b}$ and $R_{8b}$ can together form a divalent alkylene radical which is optionally interrupted by one or two divalent heteroatoms;

$R_{9b}$ is an alkyl or haloalkyl;

$R_{10b}$ is hydrogen, alkyl or haloalkyl;

$R_{11b}$ is hydrogen or alkyl radical;

$R_{12b}$ is an optionally substituted aryl or an optionally substituted heteroaryl group;

$R_{4b}$ and $R_{13b}$ represent, independently of one another, hydrogen, halogen CN or $NO_2$;

m, n, q and r represent, independently of one another, an integer equal to 0, 1 or 2;

Z represents a trivalent nitrogen atom or a C—$R_{13b}$ radical, the three other valencies of the carbon atom forming part of the aromatic ring; and (b) at least one substituted imidazole compound of the general formula (II) or a veterinarily acceptable salt thereof:

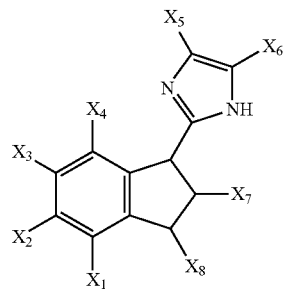

(II)

where $X_1$ is H, halogen or $CH_3$;

$X_2$ is H;

$X_3$ is H, $CH_3$, halogen, methoxy, amino, alkenyl, alkynyl or ethyl;
$X_4$ is H or $CH_3$;
$X_5$ is H or $CH_3$;
$X_6$ is H or $CH_3$;
$X_7$ is H or $CH_3$; and
$X_8$ is H;
(c) one or more veterinarily acceptable carrier(s); and
(d) optionally, at least one crystallization inhibitor.

In another embodiment of the invention, the compound of formula (II) above is combined with the 1-arylpyrazole (s) is a compound of formula (IB), wherein
$R_{1b}$ is methyl, CN or halogen;
$R_{14b}$ is $C_1$-$C_6$-alkyl or $C_1$-$C_6$-haloalkyl;
$R_{3b}$ is a hydrogen, halogen, $-NR_{7b}R_{8b}$; $-S(O)_mR_{9b}$, $-C(O)R_{9b}$, $-C(O)OR_{9b}$, $C_1$-$C_6$ alkyl, $C_1$-$C_6$ haloalkyl, $-OR_{10b}$ or $-N=C(R_{11b})(R_{12b})$;
$R_{7b}$ and $R_{8b}$ independently represent a hydrogen, $C_1$-$C_6$-alkyl, $C_1$-$C_6$ haloalkyl $-C(O)C_1$-$C_6$-alkyl, $-S(O)_rCF_3$, $C_1$-$C_6$-acyl or $C_1$-$C_6$-alkoxycarbonyl radical; or
$R_{7b}$ and $R_{8b}$ may together form a divalent alkylene radical which may be interrupted by one or two divalent hetero atoms selected from the group consisting of oxygen or sulfur;
$R_{9b}$ is a $C_1$-$C_6$-alkyl or $C_1$-$C_6$-haloalkyl radical;
$R_{10b}$ is a $C_1$-$C_6$-alkyl or $C_1$-$C_6$-haloalkyl radical or a hydrogen atom;
$R_{11b}$ is a $C_1$-$C_6$-alkyl radical or a hydrogen atom;
$R_{12b}$ is an optionally substituted phenyl or optionally substituted heteroaryl group wherein the substituents are selected from the group consisting of halogen, $-OH$, $-O-C_1$-$C_6$-alkyl, $-S-C_1$-$C_6$-alkyl, cyano and $C_1$-$C_6$-alkyl;
$R_{6b}$ is a halogen, $C_1$-$C_6$-haloalkyl, $C_1$-$C_6$-haloalkoxy, $S(O)_qCF_3$ or $SF_5$ group; and
Z is a C—$R_{13b}$ radical.

In another embodiment of invention, the compound of formula (II) above is combined with the 1-arylpyrazole(s) is a compound of formula (IB), wherein
$R_{1b}$ is methyl, CN or halogen;
$R_{2b}$ is $S(O)_nR_{14b}$;
$R_{14b}$ is $C_1$-$C_6$-alkyl or $C_1$-$C_6$-haloalkyl;
$R_{3b}$ is $-NR_{7b}R_{8b}$,
$R_{7b}$ and $R_{8b}$ independently represent a hydrogen, $C_1$-$C_6$-alkyl, $C_1$-$C_6$ haloalkyl, $-C(O)C_1$-$C_6$-alkyl, $-S(O)_rCF_3$, $C_1$-$C_6$-acyl or $C_1$-$C_6$-alkoxycarbonyl radical;
$R_{6b}$ is a halogen, $C_1$-$C_6$-haloalkyl, or $C_1$-$C_6$-haloalkoxy;
m, n, q and r represent, independently of one another, an integer equal to 0 or 1; and
Z is a C—$R_{13b}$ radical.

In still another embodiment of the invention, the compound of formula (II) above is combined with the 1-arylpyrazole(s) is a compound of formula (IB), wherein
$R_{1b}$ is CN;
$R_{2b}$ is $S(O)_nR_{14b}$;
$R_{14b}$ is $CF_3$;
$R_{3b}$ is $NR_{7b}R_{8b}$,
$R_{7b}$ and $R_{8b}$ are hydrogen;
$R_{4b}$ and $R_{13b}$ are each Cl;
$R_{6b}$ is $CF_3$.

(this compound is also known as fipronil or 1-[2,6-dichloro-4-trifluoromethyl phenyl]-3-cyano-4-trifluoromethylsulfinyl-5-amino pyrazole).

In another embodiment of the invention, the formulation comprises at least one substituted imidazole compound and at least one 1-arylpyrazole of formula (I) as described above, one or more pharmaceutically acceptable carrier(s), and optionally one or more crystallization inhibitors.

In another embodiment of the invention, the formulation comprises at least one substituted imidazole compound of formula (II) described above and at least one 1-arylpyrazole compound of formula (I) described above, one or more pharmaceutically acceptable carrier(s), and optionally one or more crystallization inhibitors.

In another embodiment of the invention, the formulation comprises the compound of formula (II) above combined with at least one 1-arylpyrazole of formula (I) wherein $R_1$ is cyano, $-C(O)R_8$, $-C(O)OR_8$, $-C(O)NR_9R_{10}$, $-C(=NOH)NH_2$, $-C(=NNH_2)$, or $-C(S)NH_2$.

In another embodiment of the formulation, the 1-arylpyrazole(s) of formula (I) is provided wherein $R_3$ is alkyl or haloalkyl.

In one embodiment of the invention, the formulation comprises the compound of formula (II) above combined with a 1-arylpyrazole(s) of formula (I) wherein:
$R_1$ is cyano, $-C(O)R_8$, $-C(O)OR_8$, $-C(O)NR_9R_{10}$, $-C(=NOH)NH_2$, $-C(=NNH_2)$, or $-C(S)NH_2$; and
$R_2$ is $-SCN$, 4-5-dicyanoimidazol-2-yl, or $-S(O)_mR_{11}$.

In another embodiment of the formulation, the compound of formula (II) above is combined with the 1-arylpyrazole(s) of formula (I) is provided wherein:
$R_1$ is cyano, $-C(O)R_8$, $-C(O)OR_8$, $-C(O)NR_9R_{10}$, $-C(=NOH)NH_2$, $-C(=NNH_2)$, or $-C(S)NH_2$;
$R_2$ is $-SCN$, 4-5-dicyanoimidazol-2-yl, or $-S(O)_mR_{11}$; and
$R_3$ is alkyl or haloalkyl.

In still another embodiment of the invention, the compound of formula (II) above is combined with the 1-arylpyrazole(s) of formula (I) is provided wherein:
$R_1$ is cyano;
$R_2$ is $-SCN$, 4-5-dicyanoimidazol-2-yl, or $-S(O)_mR_{11}$;
$R_3$ is alkyl or haloalkyl;
$R_4$, $R_5$ and $R_7$ are independently hydrogen, or halogen; and
Z is C—$R_{13}$.

In another embodiment of the invention, the formulation comprises the compound of formula (II) above combined with at least one 1-arylpyrazole(s) of formula (I) wherein:
$R_1$ is cyano;
$R_2$ is $-SCN$, 4-5-dicyanoimidazol-2-yl, or $-S(O)_mR_{11}$;
$R_3$ is $C_1$-$C_4$alkyl or $C_1$-$C_4$haloalkyl;
$R_6$ is halogen, haloalkyl or $SF_5$; and
Z is C—$R_{13}$.

In one embodiment of the invention, the formulation comprises the compound of formula (II) above combined with at least one 1-arylpyrazole(s) of formula (I) wherein:
$R_1$ is cyano;
$R_2$ is $-S(O)_mR_{11}$;
$R_3$ is $C_1$-$C_4$alkyl, $C_1$-$C_4$haloalkyl, or $NR_9R_{10}$;
$R_4$, $R_5$ and $R_7$ are independently hydrogen, or halogen;
$R_6$ is halogen, $C_1$-$C_4$alkyl, $C_1$-$C_4$haloalkyl, or $SF_5$;
Z is C—$R_{13}$; and
$R_{13}$ is halogen or $C_1$-$C_4$haloalkyl.

In another embodiment of the invention, the formulation comprises the compound of formula (II) above combined with at least one 1-arylpyrazole of formula (I) wherein:
$R_1$ is cyano;
$R_2$ is $-S(O)_mR_{11}$;
$R_3$ is methyl, ethyl, propyl, or $C_1$-$C_4$haloalkyl;
$R_4$ is halogen;
$R_5$ and $R_7$ are hydrogen;
$R_6$ is $C_1$-$C_4$haloalkyl;
Z is C—$R_{13}$;
$R_{11}$ is $-CF_3$, $-CClF_2$, or $CFCl_2$; and
$R_{13}$ is halogen.

In still another embodiment of the invention, the formulation comprises the compound of formula (II) above combined with at least one 1-arylpyrazole of formula (I) wherein:
$R_1$ is cyano;
$R_2$ is —$S(O)_m R_{11}$;
$R_3$ is methyl or ethyl;
$R_4$ is chloro or fluoro;
$R_5$ and $R_7$ are hydrogen;
$R_6$ is —$CF_3$;
Z is C—$R_{13}$;
$R_{11}$ is —$CFCl_2$; and
$R_{13}$ is chloro or fluoro.

In another embodiment of the invention the formulation comprising at least one 1-arylpyrazole and at least one substituted imidazole compound comprises at least one 1-arylpyrazole of formula (IA) as described above, or a salt thereof, a pharmaceutically or veterinarily acceptable carrier, and optionally at least one crystallization inhibitor.

In another embodiment of the invention, the formulation comprises at least one substituted imidazole of formula (II) described above and at least one 1-arylpyrazole compound of formula (IA) described above, or salts thereof, a pharmaceutically or veterinarily acceptable carrier, and optionally at least one crystallization inhibitor.

In another embodiment of the invention, the formulation comprises the compound of formula (II) above combined with at least one 1-aryl-5-alkyl pyrazole compound of formula (IA) wherein:
$R_{2a}$ is —$S(O)_m R_{11a}$;
$R_{3a}$ is methyl, or ethyl;
$R_{4a}$ is halogen;
$R_{6a}$ is $C_1$-$C_4$ haloalkyl;
$R_{13a}$ is halogen;
$R_{11a}$ is —$CF_3$, —$CClF_2$, or —$CFCl_2$; and
m is 0, 1 or 2.

In another embodiment of the invention, the formulation comprises the compound of formula (II) above combined with at least one 1-aryl-5-alkyl pyrazole compound of formula (IA) wherein:
$R_{2a}$ is —$S(O)_m R_{11a}$;
$R_{3a}$ is methyl, or ethyl;
$R_{4a}$ is halogen;
$R_{6a}$ is $C_1$-$C_4$ haloalkyl;
$R_{13a}$ is halogen;
$R_{11a}$ is —$CF_3$, —$CClF_2$, or —$CFCl_2$; and
m is 0, 1 or 2.

In still another embodiment of the invention, the compound(s) of formula (IA) is a compound wherein:
$R_{2a}$ is —$S(O)_m R_{11a}$;
$R_{3a}$ is methyl;
$R_{4a}$ is —Cl;
$R_{6a}$ is —$CF_3$;
$R_{13a}$ is —F;
$R_{11a}$ is —$CFCl_2$; and
m is 0, 1 or 2.

In still another embodiment of the invention, the substituted imidazole compound(s) in the formulation is a compound of formula (II), wherein
$X_1$ is H, halogen or $CH_3$;
$X_2$ is H;
$X_3$ is H, $CH_3$, halogen, methoxy, amino, alkenyl, alkynyl or ethyl;
$X_4$ is H or $CH_3$;
$X_5$ is H or $CH_3$;
$X_6$ is H or $CH_3$;
$X_7$ is H or $CH_3$; and
$X_8$ is H.

In another embodiment, the substituted imidazole compound(s) in the formulation is a compound of formula (II), wherein
$X_1$ is H or $CH_3$;
$X_2$ is H;
$X_3$ is H, $CH_3$, halogen or methoxy;
$X_4$ is H;
$X_5$ is H;
$X_6$ is H;
$X_7$ is H; and
$X_8$ is H.

In another embodiment of the invention, the substituted imidazole compound in the formulation is:

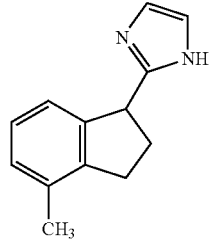

1H-imidazole, 2-(2,3-dihydro-4-methyl-1H-inden-1-yl).

In one embodiment of the invention, the 1-arylpyrazole compound is fipronil and the substituted imidazole compound is 1H-imidazole, 2-(2,3-dihydro-4-methyl-1H-inden-1-yl).

In yet another embodiment of the invention, the 1-arylpyrazole compound is fipronil and the substituted imidazole compound is as follows:

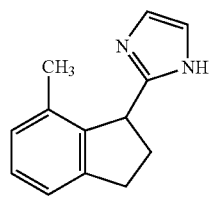

1H-imidazole, 2-(2,3-dihydro-7-methyl-1H-inden-1-yl).

With the above details in mind regarding the substituent possibilities for compounds (IA) and (IB), yet another aspect of the invention provides a composition for the treatment and prevention of parasites in an animal in need thereof which comprises:
(a) at least one 1-aryl-5-alkyl pyrazole compound of formula (IA) or (IB) as detailed above;
(b) at least one substituted imidazole compound of formula (III):

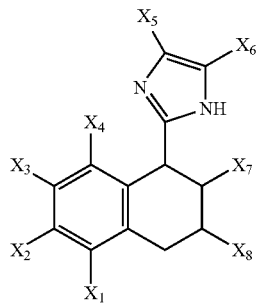

(III)

wherein:
$X_1$, $X_2$, $X_3$, $X_4$, $X_5$, $X_6$, $X_7$ and $X_8$ are as detailed above in Table 2;
(c) a veterinarily acceptable carrier; and
(d) optionally one or more crystallization inhibitors.

In another aspect, one embodiment of the invention combines at least one 1-aryl-5-alkyl pyrazole compound (e.g., fipronil) with a compound of formula (III) as follows:

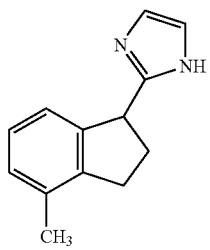

2-(5,6-dimethyl-1,2,3,4-tetrahydronaphthalen-1-yl)-1H-imidazole along with a veterinarily acceptable carrier and optionally one or more crystallization inhibitors.

Methods of Making the Compounds.

Methods for making the compounds of (IA) and (IB) are known and can be found in the references cited above regarding the 1-arylpyrazole compounds. With respect to the substituted imidazoles of compound (II) the following procedures were used.

The following synthetic route was used for 1H-imidazole, 2-(2,3-dihydro-4-methyl-1H-inden-1-yl):

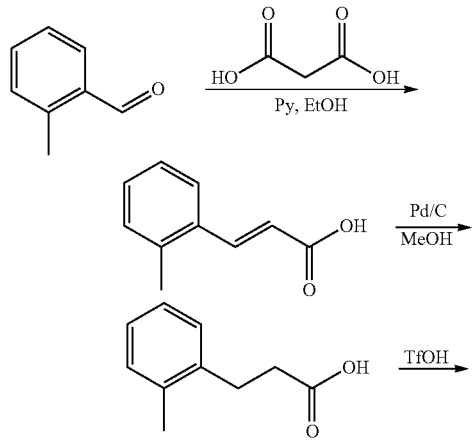

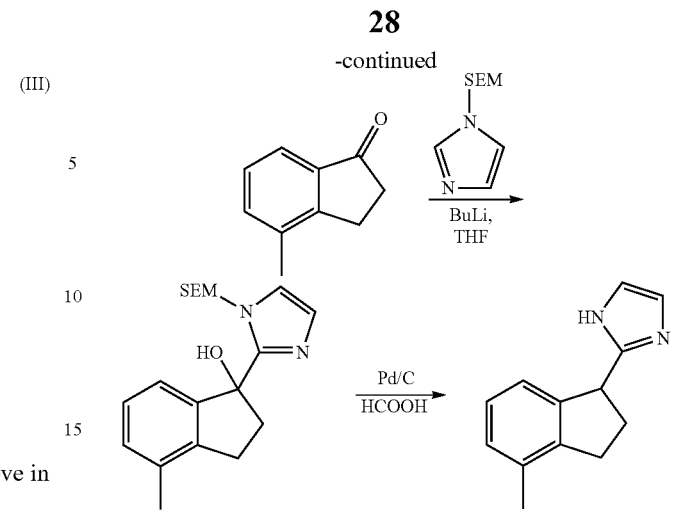

Briefly, into a 250-mL round-bottom flask, was placed a solution of 2-methylbenzaldehyde (8 g, 66.58 mmol, 1.00 equiv) in ethanol (80 mL), malonic acid (7.6 g, 73.03 mmol, 1.10 equiv), Pyridine (5 mL). The resulting solution was heated to reflux for 48 hr and allowed to cool to room temperature. The crystalline mass which formed was collect by filtration and washed with ethanol. This resulted in 6 g (55%) of (E)-3-o-tolylacrylic acid as a white solid. Next, into a 250-mL round-bottom flask was placed a solution of (E)-3-o-tolylacrylic acid (12 g, 73.99 mmol, 1.00 equiv) in methanol (80 mL), Palladium carbon (2 g, 10%). Hydrogen was bubbled into the solution and the resulting solution was stirred overnight at room temperature. The solids were filtered out and the residue was concentrated under vacuum. This resulted in 12 g (98%) of 3-o-tolylpropanoic acid as colorless oil. Next, a solution of 3-o-tolylpropanoic acid (12 g, 73.08 mmol, 1.00 equiv) in TfOH (70 mL) was placed into a 250-mL round-bottom flask. The resulting solution was stirred overnight at room temperature. Then, ice-water was added and extracted with DCM. The combined organic phases were dried over anhydrous $Na_2SO_4$. After filtration and concentration, the residue was applied onto a silica gel column with EA/PE=1/100 to 1/50. This resulted in 10.6 g (98%) of 4-methyl-2,3-dihydroinden-1-one as a white solid. Next, a solution of 1-((2-(trimethylsilyl)ethoxy)methyl)-1H-imidazole (270 mg, 1.36 mmol, 1.00 equiv) in tetrahydrofuran (15 mL) was placed into a 100-mL 3-necked round-bottom flask. This was followed by the addition of n-BuLi (0.55 mL, 2.5M) with dropwise under $N_2$ and stirred for 1 h at −70° C. To this was added 4-methyl-2,3-dihydroinden-1-one (200 mg, 1.37 mmol, 1.00 equiv) in tetrahydrofuran (5 mL) dropwise. The reaction mixture was warmed to room temperature over a period of 1 h and the mixture was continued to stir overnight at rt. Then water was added and extracted with EA. The combined organic phases were dried over anhydrous $Na_2SO_4$. After filtration and concentration, the residue was purified by MPLC. This resulted in 250 mg (53%) of 4-methyl-1-(1-((2-(trimethylsilyl)ethoxy)methyl)-1H-imidazol-2-yl)-2,3-dihydro-1H-inden-1-ol as colorless oil. Finally, a solution of 4-methyl-1-(1-((2-(trimethylsilyl)ethoxy)methyl)-1H-imidazol-2-yl)-2,3-dihydro-1H-inden-1-ol (100 mg, 0.29 mmol, 1.00 equiv) in HCOOH (10 mL), Palladium carbon (10 mg) was placed into a 100 mL round bottom flask.

The resulting solution was heated to reflux for one overnight. The pH value of the solution was adjusted to 8 with aqueous sodium bicarbonate solution and extracted with EA. The combined organic phases were dried over anhydrous Na$_2$SO$_4$. After filtration and concentration, the residue was purified by MPLC. This resulted in 40 mg (67%) of 2-(4-methyl-2,3-dihydro-1H-inden-1-yl)-1H-imidazole as a white solid. LCMS (m/e) 199 (M+H); $^1$H NMR (300 MHz, CDCl$_3$) δ ppm 6.96-7.18 (m, 3H), 6.93 (s, 2H), 4.59 (t, J=8.1 Hz, 1H), 2.80-3.00 (m, 2H), 2.50-2.62 (m, 1H), 2.29 (s, 3H), 2.45-2.29 (s, 1H).

The same synthetic route was used for 1H-imidazole, 2-(2,3-dihydro-7-methyl-1H-inden-1-yl) with the exception of using 3-methylbenzaldehyde as the starting material instead of 2-methylbenzaldehyde.

The following synthetic route was used for the substituted imidazoles of compound (III):

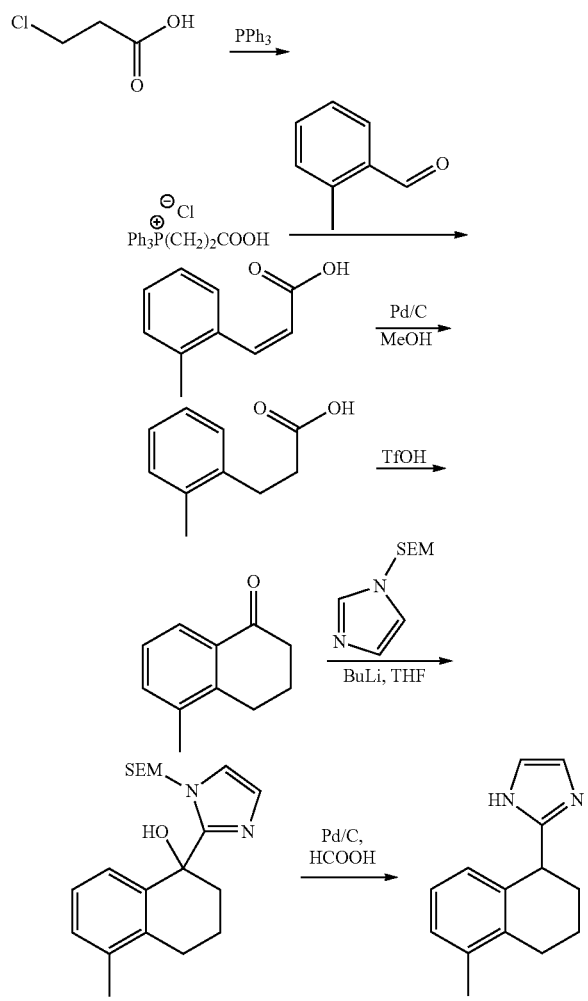

Briefly, to a solution of 2,3-dimethylbenzaldehyde (4 g, 29.81 mmol, 1.00 equiv) and (2-carboxyethyl)triphenylphosphanium chloride (12.2 g, 32.90 mmol, 1.10 equiv) in 1:1 mixture of dry THF/DMSO (100 mL) was added sodium hydride (2.2 g, 64.17 mmol, 2.10 equiv, 70%) at 0° C. The resulting solution was allowed to stir overnight at room temperature. Water was added and the aqueous layer was adidified to pH 1-2 with concentrated HCl aqueous, and extracted with ethyl acetate. The combined organic phases were dried over anhydrous Na$_2$SO$_4$. After filtration and concentration, the residue was applied onto a silica gel column with ethyl acetate/petroleum ether=1/8 to 1/2. This resulted in 2.2 g (38%) of (E)-4-(2,3-dimethylphenyl)but-3-enoic acid as a colorless solid. Next, a solution of (E)-4-(2,3-dimethylphenyl)but-3-enoic acid (3.3 g, 17.35 mmol, 1.00 equiv) in methanol (30 mL), palladium carbon (0.5 g) was placed in a 100 mL round bottom flask. Hydrogen was bubbled into the mixture and the resulting solution was stirred overnight at room temperature. The solids were filtered out and the filtrate was concentrated under reduced pressure. This resulted in 3.2 g (95%) of 4-(2,3-dimethylphenyl)butanoic acid as a white solid. After this, a solution of 4-(2,3-dimethylphenyl)butanoic acid (3.2 g, 16.64 mmol, 1.00 equiv) in TfOH (50 mL) was placed into a 100 mL round bottom flask. The resulting solution was stirred overnight at room temperature. Then, ice-water was added and extracted with DCM. The combined organic phases were dried over anhydrous Na$_2$SO$_4$. After filtration and concentration, the residue was applied onto a silica gel column with ethyl acetate/petroleum ether=1/6. This resulted in 2.4 g (82%) of 5,6-dimethyl-3,4-dihydronaphthalen-1(2H)-one as a light yellow solid. Next, a solution of 1-((2-(trimethylsilyl)ethoxy)methyl)-1H-imidazole (1.14 g, 5.75 mmol, 1.00 equiv) in tetrahydrofuran (30 mL) was placed into a 100 mL 3-necked round bottom flask. This was followed by the addition of n-BuLi (2.3 mL, 2.5M) and the reaction mixture was stirred for 1 h at −70° C. To this was added 5,6-dimethyl-3,4-dihydronaphthalen-1(2H)-one (1 g, 5.74 mmol, 1.00 equiv) at −70° C. The reaction mixture was warmed to room temperature over a period of 2 hrs. Then, water was added and extracted with EtOAc. The combined organic phases were dried over anhydrous Na$_2$SO$_4$. After filtration and concentration, the residue was purified by MPLC. This resulted in 1.5 g (69%) of 5,6-dimethyl-1-(1-((2-(trimethylsilyl)ethoxy)methyl)-1H-imidazol-2-yl)-1,2,3,4-tetrahydronaphthalen-1-ol as a white solid. LCMS (m/e) 373 (M+H); $^1$H NMR (300 MHz, CDCl$_3$) δ ppm 7.00-7.03 (m, 2H), 6.92 (d, J=7.8 Hz, 1H), 6.66 (d, J=7.8 Hz, 1H), 4.93 (s, 1H), 4.67-4.75 (m, 2H), 3.30-3.40 (m, 1H), 3.08-3.15 (m, 1H), 2.88-2.98 (m, 1H), 2.52-2.68 (m, 1H), 2.27 (s, 3H), 2.20 (s, 3H), 2.02-2.20 (m, 3H), 1.85-2.00 (m, 1H), 0.78-0.85 (m, 2H), −0.02 (s, 9H). Following this, a solution of 5,6-dimethyl-1-(1-((2-(trimethylsilyl)ethoxy)methyl)-1H-imidazol-2-yl)-1,2,3,4-tetrahydronaphthalen-1-ol (250 mg, 0.67 mmol, 1.00 equiv) in dichloromethane (5 mL), trifluoroacetic acid (5 mL) was placed into a 100 mL round bottom flask. The resulting solution was stirred for 3 h at room temperature. The pH value of the solution was adjusted to 8 with sodium bicarbonate. The resulting solution was extracted with dichloromethane and the organic layers combined and dried over anhydrous sodium sulfate. After filtration and concentration, the residue was purified by MPLC. This resulted in 30 mg (18%) of 1-(1H-imidazol-2-yl)-5,6-dimethyl-1,2,3,4-tetrahydronaphthalen-1-ol as a yellow solid. LCMS (m/e) 359 (M+H); $^1$H NMR (400 MHz, CDCl$_3$) δ ppm 7.11 (d, J=7.6 Hz, 1H), 7.02-7.12 (m, 3H), 6.78 (d, J=7.6 Hz, 1H), 5.10 (s, 1H), 4.62-4.72 (m, 2H), 3.30-3.42 (m, 1H), 3.07-3.18 (m, 1H), 2.84-2.95 (m, 1H), 2.54-2.68 (m, 1H), 2.31 (s, 3H), 2.11-2.26 (m, 3H), 1.92-2.01 (m, 1H), 0.83 (t, J=8.4 Hz, 2H), −0.02 (s, 9H). Finally, a solution of 2-(5,6-dimethyl-3,4-dihydronaphthalen-1-yl)-1H-imidazole (100 mg, 0.45 mmol, 1.00 equiv) in methanol (10 mL), Palladium carbon (20 mg, 10%) was placed into a 100 mL round bottom flask. Hydrogen was bubbled into the solution and the resulting mixture was stirred for 1 overnight at room temperature. The solids were filtered out and the residue was purified by MPLC. This resulted in 80 mg (78%) of 2-(5,6-dimethyl-1,2,3,4-tetrahydronaphthalen-1-yl)-1H-imidazole as a white solid. LCMS (m/e) 213 (M+H); $^1$H NMR (300 MHz, CDCl$_3$) δ ppm 7.02-7.15 (m, 2H), 6.86-6.95 (m, 3H), 4.39 (t, J=5.1 Hz, 1H), 2.62-2.75 (m, 2H), 2.20-2.32 (m, 1H), 2.26 (s, 3H), 2.01-2.17 (m, 1H), 1.82-1.98 (m, 1H), 1.62-1.78 (m, 1H).

Methods of Treatment

In yet another aspect of the invention, a method for preventing or treating a parasite infestation/infection in an animal is provided, comprising administering a composition comprising an effective amount of at least one 1-arylpyrazole compound of formula (IA) or (IB) together with a substituted imidazole compound of formula (II) or formula (III), along with a pharmaceutically or veterinarily acceptable carrier and optionally a crystallization inhibitor. The compositions or formulations of the invention have long-lasting efficacy against fleas and ticks and are also able to quickly eradicate flea and tick infestations.

Yet another aspect of the invention provides a method for treating or preventing a parasite infestation in an animal in need thereof comprising administering an effective amount of a composition of the invention that comprises at least one 1-arylpyrazole compound, at least one substituted imidazole compound (i.e., combinations thereof), and optionally at least one crystallization inhibitor; wherein the 1-arylpyrazole and the substituted imidazole compounds are administered in a common carrier.

By "treating" or "treat" or "treatment" is intended the application or administration of a composition of the invention to an animal that has a parasitic infestation for the eradication of the parasite or the reduction of the number of the parasites infesting the animal undergoing treatment. It is noted that the compositions of the invention may be used to prevent such a parasitic infestation.

In one embodiment of the invention, the 1-arylpyrazole compound (s) is a compound of formula (IA) or (IB). In another embodiment of the invention, the substituted imidazole compound (s) is a substituted imidazole compound of formula (II) or formula (III).

It will be appreciated by those of skill in the art that the method of the invention encompasses administering the 1-arylpyrazole compound(s) separately from the substituted imidazole compound as well as administering the 1-arylpyrazole compound(s) together with the substituted imidazole compound(s), although the two compounds may be in separate carriers. For example, the 1-arylpyrazole compound(s) may be administered at the same location on the animal as the substituted imidazole compound(s) or the 1-arylpyrazole compound(s) may be administered at a different location on the animal. Furthermore, the 1-arylpyrazole compound(s) may be administered by one mode of administration (e.g. topical, oral, parenteral, etc.) while the substituted imidazole compound(s) may be administered by a different mode of administration. The method of the invention also encompasses the administration of the 1-arylpyrazole compound(s) simultaneously with the substituted imidazole compound(s) or sequentially with the substituted imidazole compound(s) (i.e., at different times).

The following protocol is exemplary of the treatment method used to test formulations of the invention comprising a 1-arylpyrazole compound and a substituted imidazole compound of formula (II) for its effectiveness against an infestation of ticks (*Rhipicephalus sanguineus*).

The individual dog is the experimental unit of the study (Beagle; ≥12 weeks in age in good overall health). Events necessary for this study will begin no later than Day −7. The in-life phase of the study will end on Day 44.

TABLE 3

Schedule of Operations.

| Approximate Study Day | Event |
| --- | --- |
| Prior to or on Day −7 | Shampoo all dogs. Begin acclimation to the study facility. |
| Prior to or on Day −4 | Pretreatment tick infestation with ~50 ticks |
| Prior to or on Day −3 | Count ticks upon removal from all dogs available for the study. |
| Prior to or on Day −1 | Weigh animals for dose calculation purposes and allocate to Treatment Groups by pre-treatment tick counts. |
| Day −1 | Infest dogs with ~50 ticks. |
| At least once daily from Day 0 to end of trial | Observe dogs for health observations. |
| Day 0 | Administer treatment to dogs in Treatment Groups 2 & 3. |
| Day 0 (8 hour ± 1 hour after treatment) | Thumb count ticks but do not remove ticks. |
| Day 1 (24 hour ± 2 hour after treatment) | Thumb count ticks but do not remove ticks. |
| Day 2 (48 hours ± 2 hour after treatment) | Count ticks upon removal. |
| Day 7, 14, 21, 28, 35 and 42 | Infest dogs with ~50 ticks in infestation crates. |
| Day 7, 14, 21, 28, 35 and 42 (1 hour ± 30 minutes after infestation with ticks) | Remove dogs from infestation crates and count live and dead ticks in the infestation crates. |
| Day 7, 14, 21, 28, 35 and 42 (8 hour ± 1 hour after infestation with ticks) | Thumb count ticks but do not remove ticks. |
| Day 8, 15, 22, 29, 36 and 43 (24 ± 2 hour after infestation with ticks) | Thumb count ticks but do not remove ticks. |
| Day 9, 16, 23, 30, 37 and 44 (48 ± 1 hours post infestation with ticks) | Count ticks upon removal. |

Dogs will be shampooed with a non-insecticidal shampoo prior to or on Day −7. Dogs will be infested with approximately 50 *R. sanguineus* on or before Day −4 for allocation purposes. Dogs will be infested with approximately 50 *R. sanguineus* on Days −1, 7, 14, 21, 28, 35 and 42. The dogs will be held in infestation crates from the time of infestation with ticks until 1 hour (±30 minutes) after infestation. The 8 hour (±1 hour) and 24 hour (±2 hour) tick counts after treatment or infestation will be done by feeling through the hair with gloved hands and parting the hair to find and identify ticks which will be counted without removal (thumb counts) according to the Schedule of Operations. Ticks will be counted upon removal 48 (±2 hour) after treatment or infestation according to the Schedule of Operations. Both live and dead ticks left in the crates will be counted as well according to the Schedule of Operations. Personal protective equipment and equipment used for tick counts will be assigned to a treatment group, or will be disposable, and changed between treatment groups.

Dogs will be ranked by decreasing pre-treatment tick count. The dogs will be formed into 5 replicates of 3 dogs each. The 3 dogs with the highest tick count will form Replicate 1; the next 3 will form Replicate 2, and so on. Within replicates, one dog will be randomly allocated to each of the 3 treatment groups. This will be repeated with replicates 2 through 5. Investigational materials will be applied by parting the hair and applying directly to the skin in a single spot on the midline of the neck between the base of the skull and shoulder blades.

to as ML-449) was compared for efficacy against ticks with untreated dogs and with fipronil combined with amitraz as outlined above.

Treatment Groups

Dogs in Treatment Group 1 were not treated. Treatment group 2 received fipronil according to the calculation: Weight of dog (kg)×0.067 mL/kg=calculated dose. Treatment group 2 also received amitraz according to the calculation: Weight of dog (kg)×0.040 mL/kg=calculated dose. Treatment group 3 received fipronil as calculated above. Treatment group 3 also received ML-449 (i.e., 1H-imidazole, 2-(2,3-dihydro-4-methyl-1H-inden-1-yl) according to the calculation: Weight of dog (kg)×0.067 mL/kg=calculated dose.

Investigational materials will be applied by parting the hair and applying directly to the skin in a single spot on the midline of the neck between the base of the skull and shoulder blades. The fipronil and the amitraz will be applied in separate syringes with the tips of the syringes held closely together so that the material from both syringes will be applied in a single spot.

TABLE 4

Tick thumb counts for untreated dogs (treatment group 1), dogs treated with fipronil and amitraz (treatment group 2) and dogs treated with fipronil and ML-449 (treatment group 3, i.e., fipronil combined with 1H-imidazole, 2-(2,3-dihydro-4-methyl-1H-inden-1-yl)).

| Treatment Group | Thumb Counts Day 0/8 hr | Thumb Counts Day 1/24 hr | Thumb Counts Day 7/8 hr | Thumb Counts Day 8/24 hr | Thumb Counts Day 14/8 hr | Thumb Counts Day 15/24 hr | Thumb Counts Day 21/8 hr | Thumb Counts Day 22/24 hr | Thumb Counts Day 28/8 hr | Thumb Counts Day 29/24 hr | Thumb Counts Day 35/8 hr | Thumb Counts Day 36/24 hr | Thumb Counts Day 42/8 hr | Thumb Counts Day 43/24 hr |
|---|---|---|---|---|---|---|---|---|---|---|---|---|---|---|
| 1 | 24 | 17 | 22 | 12 | 35 | 11 | 29 | 25 | 21 | 15 | 21 | 17 | 15 | 10 |
| 1 | 18 | 9 | 9 | 4 | 30 | 16 | 22 | 7 | 20 | 20 | 17 | 9 | 21 | 18 |
| 1 | 9 | 6 | 21 | 13 | 14 | 13 | 15 | 7 | 10 | 10 | 14 | 10 | 21 | 16 |
| 1 | 17 | 16 | 29 | 16 | 29 | 20 | 31 | 15 | 45 | 34 | 34 | 17 | 31 | 15 |
| 1 | 13 | 11 | 15 | 10 | 18 | 12 | 17 | 7 | 12 | 6 | 19 | 4 | 16 | 8 |
| geomean | 15.4 | 11.1 | 17.9 | 10.1 | 23.9 | 14.1 | 21.9 | 10.6 | 18.8 | 14.5 | 20.1 | 10.2 | 20.1 | 12.9 |
| 2 | 14 | 2 | 0 | 0 | 1 | 0 | 13 | 0 | 10 | 0 | 16 | 2 | 18 | 4 |
| 2 | 8 | 0 | 0 | 0 | 3 | 1 | 7 | 0 | 7 | 9 | 10 | 4 | 12 | 16 |
| 2 | 2 | 0 | 0 | 0 | 5 | 0 | 9 | 0 | 10 | 4 | 10 | 5 | 16 | 4 |
| 2 | 16 | 0 | 0 | 0 | 4 | 0 | 9 | 1 | 17 | 8 | 16 | 12 | 15 | 5 |
| 2 | 18 | 12 | 0 | 0 | 0 | 0 | 0 | 0 | 7 | 2 | 7 | 3 | 10 | 4 |
| geomean | 9.6 | 1.1 | 0.0 | 0.0 | 2.0 | 0.1 | 5.5 | 0.1 | 9.7 | 3.2 | 11.3 | 4.4 | 13.9 | 5.6 |
| % Reduction | 38.1 | 90.2 | 100.0 | 100.0 | 91.7 | 98.9 | 75.1 | 98.6 | 48.5 | 77.8 | 43.8 | 56.8 | 30.9 | 56.3 |
| 3 | 21 | 8 | 0 | 0 | 7 | 0 | 4 | 0 | 10 | 0 | 24 | 8 | 4 | 1 |
| 3 | 5 | 1 | 0 | 0 | 0 | 0 | 0 | 0 | 1 | 0 | 9 | 2 | 6 | 0 |
| 3 | 9 | 0 | 0 | 0 | 0 | 0 | 0 | 0 | 0 | 0 | 5 | 0 | 21 | 4 |
| 3 | 7 | 0 | 0 | 0 | 0 | 0 | 0 | 1 | 2 | 0 | 0 | 0 | 1 | 1 |
| 3 | 18 | 7 | 0 | 0 | 0 | 0 | 1 | 0 | 1 | 0 | 2 | 0 | 1 | 0 |
| geomean | 10.5 | 1.7 | 0.0 | 0.0 | 0.5 | 0.0 | 0.6 | 0.1 | 1.7 | 0.0 | 4.4 | 0.9 | 4.0 | 0.8 |
| % Reduction | 32.0 | 84.6 | 100.0 | 100.0 | 97.8 | 100.0 | 97.3 | 98.6 | 91.2 | 100.0 | 78.2 | 90.9 | 80.2 | 93.6 |

Tick Counts

Ticks will be thumb counted at 8 hours (±1 hour) and 24 hours (±2 hours) after treatment or infestation according to the Schedule of Operations. Ticks will be counted and removed at 48 hours (±2 hours) after treatment or infestation as in the Schedule of Operations (Table 3). Tick counts will be transformed to the natural logarithm of (count+1) for calculation of geometric means by treatment group at each time point. Percent reduction from the corresponding control mean will be calculated using the formula $[(C-T)/C] \times 100$, where C=geometric mean for the control group and T=geometric mean for the treated group. A plot of the percent reduction for the treated group over the study will be constructed.

Results of Comparative Study with a Combination of Fipronil and Amitraz

A formulation of a 1-arylpyrazole (i.e., fipronil) combined with a substituted imidazole of formula (II) (i.e., 1H-imidazole, 2-(2,3-dihydro-4-methyl-1H-inden-1-yl), also referred Data from Table 4 indicates that ML-449 in combination with fipronil (treatment group 3) reduces the number of ticks thumb counted as well as fipronil and amitraz (treatment group 2). Moreover, the number of ticks thumb counted for the ML-449 group remains substantially lower than the number of ticks thumb counted for the fipronil and amitraz group out to at least 43 days (e.g., a 93.6% reduction in thumb counted ticks for ML-449 versus a 56.3% reduction in thumb counted ticks for the fipronil and amitraz treated group).

Another screening method used to test compounds of the present invention is the tick contact behavioral assay (TCBA). Compounds that elicit excitatory activity in ticks should increase their motility, thus increasing the parasite's chances of encountering fipronil if fipronil is present.

The TCBA was performed on *Rhipicephalus sanguineus* in glass vials. Briefly, a paper disc is treated with the desired amount of test compound and placed into the vial with approximately ten ticks. The ticks are observed for excitatory response but are not otherwise stimulated for evaluation.

From these observations, an $EC_{50}$ for excitatory response is established. Observations were made at 4 h and 24 h post-treatment. Compounds that demonstrated a low $EC_{50}$ for the TCBA were further tested for increased mortality in combination with fipronil. Results of the tests are as follows.

TABLE 5

TCBA and combined fipronil results for amitraz, demiditraz, and selected compounds of the invention from compound (II) (e.g., ML-449) and compound (III) (e.g., 2-(5-methyl-1,2,3,4-tetrahydronaphthalen-1-yl)-1H-imidazole).

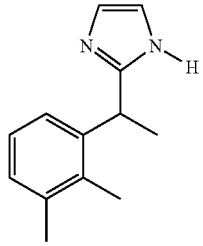

|  | Amitraz | Demiditraz racemate (Pfizer) | ML-449 | 2-(5-methyl-1,2,3,4-tetrahydronaphthalen-1-yl)-1H-imidazole |
|---|---|---|---|---|
| TCBA Assay $EC_{50}$ (@ 24 h, ppm) | 1.6 | 5 | 6 | 6 |
| Fipronil combination (25 ppm) (6 h mortality) - Dose (ppm) | 12.5 | 12.5 | 25 | 25 |

TCBA $EC_{50}$ values for ML-449 (6 ppm) and 2-(5-methyl-1,2,3,4-tetrahydronaphthalen-1-yl)-1H-imidazole (6 ppm) were comparable to those of amitraz (1.6 ppm) and demiditraz (5 ppm). The compounds were then combined with fipronil (25 ppm) and tested for 100% mortality at 6 hours. While 12.5 ppm of amitraz and demiditraz combined with fipronil produced 100% mortality in 6 hours, ML-449 and 2-(5-methyl-1,2,3,4-tetrahydronaphthalen-1-yl)-1H-imidazole required 25 ppm to produce the same effect. Another compound of formula (II) of the invention, 1H-imidazole, 2-(2,3-dihydro-7-methyl-1H-inden-1-yl), reported a TCBA $EC_{50}$ value of 6 ppm (data not shown). It has not yet been tested in combination with fipronil.

Yet another aspect of the invention is a kit for the treatment or prevention of a parasitic infestation in an animal, comprising one or more 1-arylpyrazole compound(s) combined with one or more substituted imidazole compound(s) in a common veterinarily acceptable carrier.

Furthermore, certain synergistic compositions of 1-arylpyrazoles and the substituted imidazoles of either formula (II) or formula (III) may be stored and administered using the kit without degradation for long periods of time, allowing for the superior control of parasites in animals.

The kit may include any of the 1-arylpyrazle compositions described above in one or more of the cavities, including any of the veterinarily acceptable carriers previously described.

In one embodiment, the veterinarily acceptable carrier that is combined with the 1-arylpyrazole compound(s) includes, but is not limited to, $C_1$-$C_{10}$ alcohols or esters thereof (including acetates, such as ethyl acetate, butyl acetate and the like), $C_{10}$-$C_{18}$ saturated fatty acids or esters thereof, $C_{10}$-$C_{18}$ monounsaturated fatty acids or esters thereof, monoesters or diesters of aliphatic diacids, glycerol monoesters (e.g. monoglycerides), glycerol diesters (e.g. diglycerides), glycerol triesters (e.g. triglycerides such as triacetin), glycols, glycol ethers, glycol esters or glycol carbonates, polyethylene glycols of various grades (PEGs) or monoethers, diethers, monoesters or diesters thereof (e.g. diethylene glycol monoethyl ether), or mixtures thereof.

In another embodiment, the veterinarily acceptable carrier includes, but is not limited to, acetone, acetonitrile, benzyl alcohol, ethanol, isopropanol, diisobutyl adipate, diisopropyl adipate (also known as CERAPHYL 230), butyl diglycol, dipropylene glycol n-butyl ether, ethylene glycol monoethyl ether, ethylene glycol monomethyl ether, dipropylene glycol monomethyl ether, liquid polyoxyethylene glycols, propylene glycol monomethyl ether, propylene glycol monoethyl ether, 2-pyrrolidone including N-methylpyrrolidone, diethylene glycol monoethyl ether, triacetin, butyl acetate, octyl acetate, propylene carbonate, butylene carbonate, dimethyl sulfoxide, amides including dimethylformamide and dimethylacetamide, or any combination thereof.

In another embodiment, the veterinarily acceptable carrier includes, but is not limited to, aryl ethers including alkoxybenzene compounds; carboxylic acid esters, including aliphatic and aromatic carboxylic acids such as benzoic acid esters, and compounds with multiple carboxylate groups; aliphatic ketones, saturated aliphatic ketones, cyclic ketones, or mixtures thereof.

In yet another embodiment, the veterinarily acceptable carrier includes, but is not limited to, $C_1$-$C_{10}$ carboxylic acid esters, phenyl carboxylic acid esters, carboxylic acid benzyl esters, benzoic acid $C_1$-$C_4$ alkyl esters, $C_1$-$C_6$ saturated aliphatic ketones, and mixtures thereof.

In still another embodiment, the veterinarily acceptable carrier includes, but is not limited to, methoxybenzene, butyl acetate, benzyl acetate, methyl isobutyl ketone, ethyl benzoate, benzyl benzoate, octyl acetate or mixtures thereof.

In another embodiment, the veterinarily acceptable carrier includes one or more solvent(s) with a dielectric constant of about 2 to about 30. In other embodiments of the invention, the veterinarily acceptable carrier comprises a solvent with a dielectric constant of about 2 to about 40, 2 to about 20, 5 to about 30, or 10 to about 30.

In still other embodiments, the veterinarily acceptable carrier comprises one or more solvents with a dielectric constant of about 2 to about 15 or about 3 to about 10. In still another embodiment, the dielectric constant of the one or more solvents is about 3.5 to about 10. In another embodiment, the dielectric constant of the one or more solvents is about 4 to about 6.5.

In another embodiment, the veterinarily acceptable carrier includes one or more aprotic solvents, preferably polar aprotic solvents, with dielectric constants of about 2 to about 30. In other embodiments of the invention, the veterinarily acceptable carrier comprises one or more aprotic solvent(s) with a dielectric constant of about 2 to about 40, 2 to about 20, 5 to about 30, or 10 to about 30.

In still other embodiments, the veterinarily acceptable carrier comprises one or more aprotic solvent(s) with a dielectric constant of about 2 to about 15 or about 3 to about 10. In still another embodiment, the dielectric constant of the one or more aprotic solvent(s) is about 3.5 to about 10. In another embodiment, the dielectric constant of the one or more aprotic solvent(s) is about 4 to about 6.5. In some embodiments, the solvents will be polar aprotic solvents with dielectric constants in the ranges described above.

The compositions of the invention can be in a variety of forms suitable for different forms of administration including, but are not limited to, oral formulations, injectable formulations, and topical, dermal or subdermal formulations.

The compositions of the invention may be in a form suitable for oral use, for example, as baits (see, e.g., U.S. Pat. No. 4,564,631, incorporated herein by reference), dietary supplements, troches, lozenges, chewables, tablets, hard or soft capsules, emulsions, aqueous or oily suspensions, aqueous or oily solutions, oral drench formulations, dispersible powders or granules, syrups or elixirs, enteric formulations or pastes. Compositions intended for oral use may be prepared according to any method known in the art for the manufacture of pharmaceutical compositions and such compositions may contain one or more agents selected from the group consisting of sweetening agents, bittering agents, flavoring agents, coloring agents and preserving agents in order to provide pharmaceutically elegant and palatable preparations.

Tablets may contain the active ingredient in admixture with non-toxic, pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc, the tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. Nos. 4,256,108; 4,166,452; and 4,265,874, which are incorporated herein by reference in their entirety, to form osmotic therapeutic tablets for controlled release.

Formulations for oral use may be hard gelatin capsules, wherein the active ingredient is mixed with an inert solid diluent, for example, calcium carbonate, calcium phosphate or kaolin. Capsules may also be soft gelatin capsules, wherein the active ingredient is mixed with water or miscible solvents such as propylene glycol, PEGs and ethanol, or an oil medium, for example peanut oil, liquid paraffin, or olive oil.

The compositions of the invention may also be in the form of oil-in-water or water-in-oil emulsions. The oily phase maybe a vegetable oil, for example, olive oil or arachis oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monoleate, and condensation products of the said partial esters with ethylene oxide, for example, polyoxyethylene sorbitan monooleate. The emulsions may also contain sweetening agents, bittering agents, flavoring agents, or preservatives.

In one embodiment of the formulation, the composition of the invention is in the form of a microemulsion. Microemulsions are well suited as the liquid carrier vehicle. Microemulsions are quaternary systems comprising an aqueous phase, an oily phase, a surfactant and a cosurfactant. They are translucent and isotropic liquids. Microemulsions are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously.

In one embodiment of the oily phase, the oily phase can be formed from mineral or vegetable oils, from unsaturated polyglycosylated glycerides or from triglycerides, or alternatively from mixtures of such compounds. In one embodiment of the oily phase, the oily phase comprises of triglycerides. In another embodiment of the oily phase, the triglycerides are medium-chain triglycerides, for example $C_8$-$C_{10}$ caprylic/capric triglyceride. Another embodiment of the oily phase will represent a % v/v range selected from the group consisting of about 2 to about 15%; about 7 to about 10%; and about 8 to about 9% v/v of the microemulsion.

The aqueous phase includes, for example water or glycol derivatives, such as propylene glycol, glycol ethers, polyethylene glycols or glycerol. In one embodiment of the glycol derivatives, the glycol is selected from the group consisting of propylene glycol, diethylene glycol monoethyl ether, dipropylene glycol monoethyl ether and mixtures thereof. Generally, the aqueous phase will represent a proportion from about 1 to about 4% v/v in the microemulsion.

Surfactants for the microemulsion include diethylene glycol monoethyl ether, dipropyelene glycol monomethyl ether, polyglycolyzed $C_8$-$C_{10}$ glycerides or polyglyceryl-6 dioleate. In addition to these surfactants, the cosurfactants include short-chain alcohols, such as ethanol and propanol.

Some compounds are common to the three components discussed above, i.e., aqueous phase, surfactant and cosurfactant. However, it is well within the skill level of the practitioner to use different compounds for each component of the same formulation. In one embodiment for the amount of surfactant/cosurfactant, the cosurfactant to surfactant ratio will be from about 1/7 to about 1/2. In another embodiment for the amount of cosurfactant, the ratio will be from about 25 to about 75% v/v of surfactant and from about 10 to about 55% v/v of cosurfactant in the microemulsion.

Oily suspensions may be formulated by suspending the active ingredient in a vegetable oil, for example, atachis oil, olive oil, sesame oil or coconut oil, or in mineral oil such as liquid paraffin. The oily suspensions may contain a thickening agent, for example, beeswax, hard paraffin or cetyl alcohol. Sweetening agents such as sucrose, saccharin or aspartame, bittering agents, and flavoring agents may be added to provide a palatable oral preparation. These compositions may be preserved by the addition of an anti-oxidant such as ascorbic acid or other known preservatives.

Aqueous suspensions may contain the active material in admixture with excipients suitable for the manufacture of aqueous suspensions. Such excipients are suspending agents, for example, sodium carboxymethylcellulose, methylcellulose, hydroxy-propylmethylcellulose, sodium alginate, polvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents or bittering agents, such as those set forth above.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, may also be present.

Syrups and elixirs may be formulated with sweetening agents, for example, glycerol, propylene glycol, sorbitol or sucrose. Such formulations may also contain a demulcent, a preservative, flavoring agent(s) or coloring agent(s).

In another embodiment of the invention, the composition can be in paste form. Examples of embodiments in a paste form include but are not limited to those described in U.S. Pat. Nos. 6,787,342 and 7,001,889, both of which are incorporated herein by reference. In addition to the active agent of the invention, the paste can also contain fumed silica; a viscosity modifier; a carrier; optionally, an absorbent; and optionally, a colorant, stabilizer, surfactant, or preservative.

The process for preparing a paste formulation comprises the steps of:
(a) dissolving or dispersing the active agent into the carrier by mixing;
(b) adding the fumed silica to the carrier containing the dissolved active agent compound and mixing until the silica is dispersed in the carrier;
(c) allowing the intermediate formed in (b) to settle for a time sufficient in order to allow the air entrapped during step (b) to escape; and
(d) adding the viscosity modifier to the intermediate with mixing to produce a uniform paste.

The above steps are illustrative, but not limiting. For example, step (a) can be the last step.

In one embodiment of the formulation, the formulation is a paste containing the active agent compound, fumed silica, a viscosity modifier, an absorbent, a colorant; and a hydrophilic carrier which is a triacetin, a monoglyceride, a diglyceride, or a triglyceride. The paste may also include a viscosity modifier including, but is not limited to, PEG 200, PEG 300, PEG 400, PEG 600, monoethanolamine, triethanolamine, glycerol, propylene glycol, polyoxyethylene (20) sorbitan mono-oleate (polysorbate 80 or Tween 80), or polyoxamers (e.g., Pluronic L 81); an absorbent including, but not limited to, magnesium carbonate, calcium carbonate, starch, or cellulose and its derivatives.

Colorants may be added to the inventive formulations. Colorants contemplated by the present invention are those commonly known in the art. Specific colorants include, for example, dyes, FD&C Blue #1 Aluminum Lake, caramel, colorant based upon iron oxide or a mixture of any of the foregoing. Especially preferred are organic dyes and titanium dioxide. Preferred ranges include from about 0.5% to about 25%.

The compositions may be in the form of a sterile injectable solutions or aqueous or oleagenous suspensions. These suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. Preservatives, such as phenol or benzyl alcohol, may be used.

In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Topical, dermal and subdermal formulations can include emulsions, creams, ointments, gels, pastes, powders, shampoos, pour-on formulations, ready-to-use formulations, spot-on solutions and suspensions. Topical application of an inventive compound or of a composition including at least one inventive compound among active agent(s) therein, a spot-on composition, can allow for the inventive compound to be distributed through the glands (e.g., sebaceous glands) of the animal or allow active agent(s) to achieve a systemic effect (plasma concentration) or throughout the haircoat. When the compound is distributed throughout glands, the glands can act as a reservoir, whereby there can be a long-lasting, e.g. 1-2 months effect or longer. Cotchet and co-workers reported the distribution of fipronil, a 1-arylpyrazole compound, to the stratum corneum, the viable epidermis and the sebaceous glands and epithelial layers of beagle dogs after spot-on administration (see Cochet et al., *Eur. J. Drug Metab. Pharmacokinet.*, 1997, 22(3), 211-216). Using $^{14}$C radiolabeled drug, the publication demonstrated that fipronil is displaced from the point of application and distributed to the whole skin, where it was persistently detected for up to 56 days after treatment. Spot-on formulations are typically applied in a localized region which refers to an area other than the entire animal. In one embodiment of a localized region, the location is between the shoulders. In another embodiment, the localized region is a stripe, e.g., a stripe from head to tail of the animal.

Pour-on formulations are described, for example, in U.S. Pat. No. 6,010,710, which is incorporated herein by reference. The pour-on formulations are advantageously oily, and generally comprise a diluent or vehicle and also a solvent (e.g. an organic solvent) for the active ingredient if the latter is not soluble in the diluent. Pour-on formulation may be administered to livestock animals such as cattle and sheep. In one embodiment, the process comprises applying the solution to livestock animals before they arrive in the Feed Lot, it being possible for this application to be the final one before the animals are slaughtered.

The compositions of the invention can also be formed in a collar such as those described in U.S. Pat. No. 5,885,607, which is incorporated herein by reference. Within the scope of the invention, matrices usually used to make collars may be used. In one embodiment of the collars which may be mentioned are matrices based on PVC (polyvinyl chloride), as described in U.S. Pat. Nos. 3,318,769; 3,852,416; 4,150,109 and 5,437,869, (all incorporated by reference) and other vinyl polymers.

The plasticizers may be chosen in particular from adipates, phthalates, phosphates and citrates. In another embodiment of the collar, one or more plasticizers are also added to the PVC, these plasticizers being chosen in particular from the following compounds: diethyl phthalate, dioctyl sebacate, dioctyl adipate, diisodecyl phthalate, acetyl tributyl citrate, diethyl hexyl phthalate, di-n-butyl phthalate, benzyl butyl phthalate, acetyl tributyl citrate, tricresyl phosphate, and 2-ethylhexyl diphenyl phosphate.

In another embodiment of the collar, a PVC matrix will be used in the presence of a primary remanent plasticizer and a secondary plasticizer, in particular according to EP 0 539 295 and EP 0 537 998.

Among the secondary plasticizers, mention may be made of the following products: acetyl triethyl citrate, triethyl citrate, triacetin, diethylene glycol monoethyl ether, triphenyl phosphate. A common stabilizer may also be added thereto.

For the purposes of the present invention, the term external device should be understood to refer to any device which can be attached externally to the animal in order to provide the same function as a collar.

In one embodiment of the invention, the combination of 1-arylpyrazole and substituted imidazole is present in the formulation at a concentration of about 2% to about 55% (w/v); about 10% to about 35% w/v; or about 18% to about 27% w/v. In another embodiment of the invention, the amount of 1-arylpyrazole is present in the formulation as a concentration of about 1% to about 25% (w/v); about 5% to about 15% (w/v); or about 8% to about 12% (w/v).

In another embodiment of the invention, the amount of substituted imidazole in the formulations is about 1% to about 30 (w/v); about 5% to about 20% (w/v); or about 10% to about 15% (w/v).

The veterinarily acceptable carrier will generally comprise a diluent or vehicle and also a solvent (e.g., an organic solvent) for the active ingredient if the latter is not soluble, not stable or is degraded in the diluent.

Organic solvents that can be used in the invention include those described above, and include but are not limited to: acetyltributyl citrate, oleic acid, fatty acid esters such as the dimethyl ester, diisobutyl adipate, diisopropyl adipate (also known as CERAPHYL 230), ketones including acetone, methylisobutyl ketone (MIK) and methyl ethyl ketone and the like, acetonitrile, benzyl alcohol, methanol, ethyl alcohol, isopropanol, butanol, aromatic ethers such as anisole, butyl diglycol, amides including dimethylacetamide and dimethylformamide, dimethyl sulfoxide, propylene glycol monomethyl ether, propylene glycol monoethyl ether, dipropylene glycol n-butyl ether, ethylene glycol monoethyl ether, ethylene glycol monomethyl ether, monomethylacetamide, dipropylene glycol monomethyl ether, liquid polyoxyethylene glycols, propylene glycol, 2-pyrrolidone including N-methylpyrrolidone, diethylene glycol monoethyl ether, ethylene glycol, triacetin, $C_1$-$C_{10}$ esters of carboxylic acids such as butyl or octyl acetate, benzyl acetate, aryl esters including benzyl benzoate, ethyl benzoate and the like, propylene carbonate, butylene carbonate, and diethyl phthalate, or a mixture of at least two of these solvents.

In one embodiment of the invention, the pharmaceutically or veterinarily acceptable carrier of the formulation comprises $C_1$-$C_{10}$ alcohols or esters thereof (including acetates, such as ethyl acetate and the like), $C_{10}$-$C_{18}$ saturated fatty acids or esters thereof, $C_{10}$-$C_{18}$ monounsaturated fatty acids or esters thereof, monoesters or diesters of aliphatic diacids, glycerol monoesters (e.g. monoglycerides), glycerol diesters (e.g. diglycerides), glycerol triesters (e.g. triglycerides such as triacetin), glycols, glycol ethers, glycol esters or glycol carbonates, polyethylene glycols of various grades (PEGs) or monoethers, diethers, monoesters or diesters thereof (e.g. diethylene glycol monoethyl ether), or mixtures thereof.

In another embodiment of the invention, the organic solvents may comprise diisopropyl adipate, dipropylene glycol monomethyl ether, propylene glycol monomethyl ether, 2-pyrrolidone including N-methylpyrrolidone, diethylene glycol monoethyl ether, triacetin, butyl acetate, octyl acetate, propylene carbonate, oleic acid, or a mixture of at least two of these solvents.

In one embodiment, solvents include $C_1$-$C_{10}$ esters of carboxylic acids such as butyl or octyl acetate.

Other solvents include diethyleneglycol monoethyl ether, triacetin, butyl acetate and octyl acetate, and mixtures thereof.

In some embodiments, the organic solvent will have a dielectric constant of between about 2 to about 35, between about 10 to about 35, or between about 20 to about 30. In other embodiments, the solvent will have a dielectric constant of between about 2 and about 20, or between about 2 and about 10. The content of this organic solvent in the overall composition will represent the complement to 100% of the composition. As discussed above, the organic solvents with dielectric constants within these ranges will typically be aprotic solvents, such as polar aprotic solvents.

The carrier may comprise a mixture of solvents. In one embodiment, the formulations comprise an organic solvent and an organic co-solvent. In some embodiments, the formulations comprise a co-solvent having a boiling point of below about 300° C. or below about 250° C. In other embodiments, the co-solvent has a boiling point of below about 200° C., or below about 130° C. In other embodiments, the co-solvent has a dielectric constant of between about 2 to about 40 or between about 10 to about 40. In other embodiments, the co-solvent has a dielectric constant of between about 20 to about 30. In still another embodiment of the invention, the co-solvent has a dielectric constant of between about 2 to about 10.

When the formulations comprise an organic solvent and a co-solvent, in some embodiments the co-solvent may be present in the composition in an organic co-solvent/organic solvent weight/weight (W/W) ratio of between about 1/15 to about 1/2. In some embodiments, the co-solvent is volatile so as to act as a drying promoter, and is miscible with the organic solvent and may or may not be miscible with water.

The solvent will be used in proportion with the concentration of the active agent compound and its solubility in this solvent. It will be sought to have the lowest possible volume. The vehicle makes up the difference to 100%.

A vehicle or diluent can be dimethyl sulfoxide (DMSO), glycol derivatives such as, for example, propylene glycol, glycol ethers, polyethylene glycols or glycerol. As vehicle or diluent, mention may also be made of plant oils such as, but not limited to soybean oil, groundnut oil, castor oil, corn oil, cotton oil, olive oil, grape seed oil, sunflower oil, etc.; mineral oils such as, but not limited to, petrolatum, paraffin, silicone, etc.; aliphatic or cyclic hydrocarbons or alternatively, for example, medium-chain (such as $C_8$ to $C_{12}$) triglycerides.

In another embodiment of the invention, an emollient or spreading or film-forming agent will be added. One embodiment of the emollient or spreading or film-forming agents are those agents selected from the group consisting of:

(a) polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, silicone oils, polydiorganosiloxane oils (such as polydimethylsiloxane (PDMS) oils), for example those containing silanol functionalities, or a 45V2 oil, (b) anionic surfactants such as alkaline stearates, sodium, potassium or ammonium stearates; calcium stearate, triethanolamine stearate; sodium abietate; alkyl sulfates (e.g. sodium lauryl sulfate and sodium cetyl sulfate); sodium dodecylbenzenesulphonate, sodium dioctylsulphosuccinate; fatty acids (e.g. those derived from coconut oil), (c) cationic surfactants such as water-soluble quaternary ammonium salts of formula $N^+R'R''R'''R''''Y^-$, in which the R radicals are optionally hydroxylated hydrocarbon radicals and $Y^-$ is an anion of a strong acid such as the halide, sulfate and sulphonate anions; cetyltrimethylammonium bromide is among the cationic surfactants which can be used, (d) amine salts of formula $N^+R'R''R'''$ in which the R radicals are optionally hydroxylated hydrocarbon radicals; octadecylamine hydrochloride is among the cationic surfactants which can be used, (e) nonionic surfactants such as sorbitan esters, which are optionally polyoxyethylenated (e.g. polysorbate 80), polyoxyethylenated alkyl ethers; polyoxypropylated fatty alcohols such as polyoxypropylene-styrol ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, (f) amphoteric surfactants such as the substituted lauryl compounds of betaine, and (g) a mixture of at least two of these agents.

In one embodiment of the amount of emollient, the emollient is used in a proportion selected from the group consisting of from about 0.1 to about 10%, and about 0.25 to about 5%, by volume.

In another embodiment of the invention, the composition can be in ready-to-use solution form as is described, for example, in U.S. Pat. No. 6,395,765, which is incorporated herein by reference. In addition to the active agent compound, the ready-to-use solution can contain a crystallization inhibitor, an organic solvent and an organic co-solvent.

In some embodiments, the crystallization inhibitor can be present in a proportion of about 1 to about 30% (w/v). Typically, the crystallization inhibitor may be present in a proportion of about 1% to about 20% (w/v) or about 5% to about 15% (w/v). Acceptable inhibitors are those whose addition to the formulation inhibits the formation of crystals when the formulation is applied. In some embodiments, formulations may include compounds that function as crystallization inhibitors other than those listed herein. In these embodiments, the suitability of a crystallization inhibitor may be determined by testing if it will sufficiently inhibit the formation of crystals so that a sample containing 10% (w/v) of the 1-arylpyrazole in a solvent as described above with 10% (w/v) of the crystallization inhibitor will result in less than 20, preferably less than 10 crystals when placed on a glass slide at 20° C. for 24 hours.

Crystallization inhibitors which are useful for the invention include but are not limited to:

(a) polyvinylpyrrolidone, polyvinyl alcohols, copolymers of vinyl acetate and of vinylpyrrolidone, 2-pyrrolidone including N-methylpyrrolidone, dimethylsufoxide, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and polymers derived from acrylic monomers, a solvent as described herein that inhibits the crystallization of the active agent, and others;

(b) anionic surfactants, such as alkaline stearates (e.g. sodium, potassium or ammonium stearate); calcium stearate or triethanolamine stearate; sodium abietate; alkyl sulfates, which include but are not limited to sodium lauryl sulfate and sodium cetyl sulfate; sodium dodecylbenzenesulphonate or sodium dioctyl sulphosuccinate; or fatty acids (e.g. coconut oil);

(c) cationic surfactants, such as water-soluble quaternary ammonium salts of formula $N^+R'R''R'''R''''Y^-$, in which the R radicals are identical or different optionally hydroxylated hydrocarbon radicals and $Y^-$ is an anion of a strong acid, such as halide, sulfate and sulphonate anions; cetyltrimethylammonium bromide is one of the cationic surfactants which can be used;

(d) amine salts of formula $N^+R'R''R'''$, in which the R radicals are identical or different optionally hydroxylated hydrocarbon radicals; octadecylamine hydrochloride is one of the cationic surfactants which can be used;

(e) non-ionic surfactants, such as optionally polyoxyethylenated esters of sorbitan, e.g. Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide;

(f) amphoteric surfactants, such as substituted lauryl compounds of betaine; or (g) a mixture of at least two of the compounds listed in (a)-(f) above.

In one embodiment of the crystallization inhibitor, a crystallization inhibitor pair will be used. Such pairs include, for example, the combination of a film-forming agent of polymeric type and of a surface-active agent. These agents can be selected from the compounds mentioned above as crystallization inhibitor.

In one embodiment of the film-forming agent, the agents are of the polymeric type which include but are not limited to the various grades of polyvinylpyrrolidone, polyvinyl alcohols, and copolymers of vinyl acetate and of vinylpyrrolidone.

In one embodiment of the surface-active agents, the agents include but are not limited to those made of non-ionic surfactants. In another embodiment of the surface active agents, the agent is a polyoxyethylenated esters of sorbitan. In yet another embodiment of the surface-active agent, the agents include the various grades of polysorbate, for example Polysorbate 80.

In another embodiment of the invention, the film-forming agent and the surface-active agent can be incorporated in similar or identical amounts within the limit of the total amounts of crystallization inhibitor mentioned above.

The pair thus constituted secures, in a noteworthy way, the objectives of absence of crystallization on the coat and of maintenance of the cosmetic appearance of the skin or fur, that is to say without a tendency towards sticking or towards a sticky appearance, despite the high concentration of active material.

The formulation can also comprise an antioxidizing agent intended to inhibit oxidation in air, this agent being present in a proportion selected from a range consisting of about 0.005 to about 1% (w/v), and about 0.01 to about 0.05% (w/v).

In one embodiment of the antioxidizing agents, the agents are those conventional in the art and include, but are not limited to, butylated hydroxyanisole, butylated hydroxytoluene, ascorbic acid, sodium metabisulphite, propyl gallate, sodium thiosulfate or a mixture of not more than two of them.

The formulation adjuvants are well known to the practitioner in this art and may be obtained commercially or through known techniques. These concentrated compositions are generally prepared by simple mixing of the constituents as defined above. Advantageously, the starting point is to mix the active material in the main solvent and then the other ingredients or adjuvants are added.

The volume applied is not restricted as long as the amount of substance administered is shown to be safe and efficacious. Typically, the volume applied depends on the size and weight of the animal as well as the concentration of active, the extent of infestation by parasites and the type of administration. The volume applied is typically of the order of about 0.3 to about 1 ml, or about 0.3 ml to about 5 ml, or about 0.3 ml to about 10 ml. In other embodiments, the volume may be about 4 ml to about 7 ml. For larger animals, the volume may be higher including, but not limited to, up to 10 ml, up to 20 ml or up to 30 ml, or higher. In one embodiment of the volume, the volume is on the order of about 0.5 ml to about 1 ml for cats, and on the order of about 0.3 to about 3 ml or 4 ml for dogs, depending on the weight of the animal.

In another embodiment of the invention, application of a spot-on formulation according to the present invention can also provide long-lasting and broad-spectrum efficacy when the solution is applied to the mammal or bird. The spot-on formulations provide for topical administration of a concentrated solution, suspension, microemulsion or emulsion for intermittent application to a spot on the animal, generally between the two shoulders (solution of spot-on type).

Spot-on formulations are well known techniques for topically delivering an antiparasitic agent to a limited area of the host. For example, U.S. Pat. Nos. 5,045,536 6,426,333; 6,482,425; 6,962,713; and 6,998,131, all incorporated herein by reference, describe spot-on formulations. WO 01/957715, also incorporated herein by reference, describes a method for controlling ectoparasites in small rodents as well as interrupting or preventing the diseases caused by arthropods or small rodents, which comprise applying topical formulations, such as spot-on compositions, to the skin, or hair of the rodents.

For spot-on formulations, the carrier can be a liquid carrier vehicle as described, for example, in U.S. Pat. No. 6,426,333. Liquid carriers for spot-on formulations include the organic solvents and co-solvents described above, among other solvents known in the art.

The liquid carrier vehicle can optionally contain a crystallization inhibitor such as the crystallization inhibitors described above, or mixtures thereof.

Spot-on formulations, described for example in U.S. Pat. No. 7,262,214 (incorporated herein by reference), may be prepared by dissolving the active ingredients into the pharmaceutically or veterinary acceptable vehicle. Alternatively, the spot-on formulation can be prepared by encapsulation of the active ingredient to leave a residue of the therapeutic agent on the surface of the animal. These formulations will vary with regard to the weight of the therapeutic agent in the combination depending on the species of host animal to be treated, the severity and type of infection and the body weight of the host.

Dosage forms may contain from about 0.5 mg to about 5 g of an active agent. In one embodiment of the dosage form, the dosage is from about 1 mg to about 500 mg of an active agent, typically about 25 mg, about 50 mg, about 100 mg, about 200 mg, about 300 mg, about 400 mg, about 500 mg, about 600 mg, about 800 mg, or about 1000 mg.

Additional veterinary/pharmaceutical active ingredients may be used with the compositions of the invention. In some embodiments, the additional active agents may include, but are not limited to, acaricides, anthelmintics, anti-parasitics and insecticides. Anti-parasitic agents can include both ectoparasiticidal and endoparasiticidal agents.

Veterinary pharmaceutical agents that may be included in the compositions of the invention are well-known in the art (see e.g. *Plumb' Veterinary Drug Handbook*, $5^{th}$ Edition, ed. Donald C. Plumb, Blackwell Publishing, (2005) or *The Merck Veterinary Manual*, $9^{th}$ Edition, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albendazole, albuterol sulfate, alfentanil, allopurinol, alprazolam, altrenogest, amantadine, amikacin sulfate, aminocaproic acid, aminopentamide hydrogen sulfate, aminophylline/theophylline, amiodarone, amitriptyline, amlodipine besylate, ammonium chloride, ammonium molybdenate, amoxicillin, clavulanate potassium, amphotericin B desoxycholate, amphotericin B lipid-based, ampicillin, amprolium, antacids (oral), antivenin, apomorphione, apramycin sulfate, ascorbic acid, asparaginase, aspiring, atenolol, atipamezole, atracurium besylate, atropine sulfate, aurnofin, aurothioglucose, azaperone, azathioprine, azithromycin, baclofen, barbituates, benazepril, betamethasone, bethanechol chloride, bisacodyl, bismuth subsalicylate, bleomycin sulfate, boldenone undecylenate, bromides, bromocriptine mesylate, budenoside, buprenorphine, buspirone, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, chlorsulon, cefoperazone sodium, cefotaxime sodium, cefotetan disodium, cefoxitin sodium, cefpodoxime proxetil, ceftazidime, ceftiofur sodium, ceftiofur, ceftiaxone sodium, cephalexin, cephalosporins, cephapirin, charcoal (activated), chlorambucil, chloramphenicol, chlordiazepoxide, chlordiazepoxide+/−clidinium bromide, chlorothiazide, chlorpheniramine maleate, chlorpromazine, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol, clindamycin, clofazimine, clomipramine, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine, dexamethasone, dexpanthenol, dexraazoxane, dextran, diazepam, diazoxide (oral), dichlorphenamide, diclofenac sodium, dicloxacillin, diethylcarbamazine citrate, diethylstilbestrol (DES), difloxacin, digoxin, dihydrotachysterol (DHT), diltiazem, dimenhydrinate, dimercaprol/BAL, dimethyl sulfoxide, dinoprost tromethamine, diphenylhydramine, disopyramide phosphate, dobutamine, docusate/DSS, dolasetron mesylate, domperidone, dopamine, doramectin, doxapram, doxepin, doxorubicin, doxycycline, edetate calcium disodium. calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (oxyglobin®), heparin, hetastarch, hyaluronate sodium, hydrazaline, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inaminone lactate, insulin, interferon alfa-2a (human recombinant), iodide (sodium/potassium), ipecac (syrup), ipodate sodium, iron dextran, isoflurane, isoproterenol, isotretinoin, isoxsuprine, itraconazole, ivermectin, kaolin/pectin, ketamine, ketoconazole, ketoprofen, ketorolac tromethamine, lactulose, leuprolide, levamisole, levetiracetam, levothyroxine sodium, lidocaine, lincomycin, liothyronine sodium, lisinopril, lomustine (CCNU), lufenuron, lysine, magnesium, mannitol, marbofloxacin, mechlorethamine, meclizine, mecofenamic acid, medetomidine, medium chain triglycerides, medroxyprogesterone acetate, megestrol acetate, melarsomine, melatonin, meloxican, melphalan, meperidine, mercaptopurine, meropenem, metformin, methadone, methazolamide, methenamine mandelate/hippurate, methimazole, methionine, methocarbamol, methohexital sodium, methotrexate, methoxyflurane, methylene blue, methylphenidate, methylprednisolone, metoclopramide, metoprolol, metronidaxole, mexiletine, mibolerlone, midazolam milbemycin oxime, mineral oil, minocycline, misoprostol, mitotane, mitoxantrone, morphine sulfate, moxidectin, naloxone, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxibutynin chloride, oxymorphone, oxytretracycline, oxytocin, pamidronate disodium, pancreplipase, pancuronium bromide, paromomycin sulfate, parozetine, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine, pheylbutazone, phenylephrine, phenypropanolamine, phenyloin sodium, pheromones, parenteral phosphate, phytonadione/vitamin K-1, pimobendan, piperazine, pirlimycin, piroxicam, polysulfated glycosaminoglycan, ponazuril, potassium chloride, pralidoxime chloride, prazosin, prednisolone/prednisone, primidone, procainamide, procarbazine, prochlorperazine, propantheline bromide, propionibacterium acnes injection, propofol, propranolol, protamine sulfate, pseudoephedrine, psyllium hydrophilic mucilloid, pyridostigmine bromide, pyrilamine maleate, pyrimethamine, quinacrine, quinidine, ranitidine, rifampin, s-adenosyl-methionine (SAMe), saline/hyperosmotic laxative, selamectin, selegiline/l-deprenyl, sertraline, sevelamer, sevoflurane, silymarin/milk thistle, sodium bicarbonate, sodium polystyrene sulfonate, sodium stibogluconate, sodium sulfate, sodum thiosulfate, somatotropin, sotalol, spectinomycin, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline, terbutaline sulfate, testosterone, tetracycline, thiacetarsamide sodium, thiamine, thioguanine, thiopental sodium, thiotepa, thyrotropin, tiamulin, ticarcilin disodium, tiletamine/zolazepam, tilmocsin, tiopronin, tobramycin sulfate, tocamide, tolazoline, telfenamic acid, topiramate, tramadol, trimcinolone acetonide, trientine, trilostane, trimepraxine tartrate w/prednisolone, tripelennamine, tylosin, urdosiol, valproic acid, vanadium, vancomycin, vasopressin, vecuronium bromide, verapamil, vinblastine sulfate, vincristine sulfate, vitamin E/selenium, warfarin sodium, xylazine, yohimbine, zafirlukast, zidovudine (AZT), zinc acetate/zinc sulfate, zonisamide and mixtures thereof.

In one embodiment of the invention, other arylpyrazole compounds such as phenylpyrazoles described above in the Background section are known in the art and are suitable for combination with the 1-aryl-5-alkyl pyrazole compounds of the invention. Examples of such arylpyrazole compounds include but are not limited to those described in U.S. Pat. Nos. 6,001,384; 6,010,710; 6,083,519; 6,096,329; 6,174,540; 6,685,954 and 6,998,131 (all of which are incorporated herein by reference, each assigned to Merial, Ltd., Duluth, Ga.).

In another embodiment of the invention, one or more macrocyclic lactones or lactams, which act as an acaricide, anthelmintic agent or insecticide, can be added to the compositions of the invention.

The macrocyclic lactones include, but are not limited to, avermectins, such as abamectin, dimadectin, doramectin, emamectin, eprinomectin, ivermectin, latidectin, lepimectin, selamectin, ML-1,694,554 and milbemycins, such as milbemectin, milbemycin D, moxidectin and nemadectin. Also included are the 5-oxo and 5-oxime derivatives of said avermectins and milbemycins. Examples of combinations of arylpyrazole compounds with macrocyclic lactones include but are not limited to those described in U.S. Pat. Nos. 6,426,333; 6,482,425; 6,962,713 and 6,998,131 (all incorporated herein by reference—each assigned to Merial, Ltd., Duluth, Ga.).

The macrocyclic lactone compounds are known in the art and can easily be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag., or Albers-Schönberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054.

Macrocyclic lactones are either natural products or are semi-synthetic derivatives thereof. The structure of the avermectins and milbemycins are closely related, e.g., by sharing a complex 16-membered macrocyclic lactone ring. The natural product avermectins are disclosed in U.S. Pat. No. 4,310,519 and the 22,23-dihydro avermectin compounds are disclosed in U.S. Pat. No. 4,199,569. Mention is also made of U.S. Pat. Nos. 4,468,390, 5,824,653, EP 0 007 812 A1, U.K. Patent Specification 1 390 336, EP 0 002 916, and New Zealand Patent No. 237 086, inter alia. Naturally occurring milbemycins are described in U.S. Pat. No. 3,950,360 as well as in the various references cited in "The Merck Index" 12th ed., S. Budavari, Ed., Merck & Co., Inc. Whitehouse Station, N.J. (1996). Latidectin is described in the "International Nonproprietary Names for Pharmaceutical Substances (INN)", *WHO Drug Information*, vol. 17, no. 4, pp. 263-286, (2003). Semisynthetic derivatives of these classes of compounds are well known in the art and are described, for example, in U.S. Pat. Nos. 5,077,308, 4,859,657, 4,963,582, 4,855,317, 4,871, 719, 4,874,749, 4,427,663, 4,310,519, 4,199,569, 5,055,596, 4,973,711, 4,978,677, 4,920,148 and EP 0 667 054.

In another embodiment of the invention, the class of acaricides or insecticides known as insect growth regulators (IGRs) can also be added to the compositions of the invention. Compounds belonging to this group are well known to the practitioner and represent a wide range of different chemical classes. These compounds all act by interfering with the development or growth of the insect pests. Insect growth regulators are described, for example, in U.S. Pat. Nos. 3,748, 356, 3,818,047, 4,225,598, 4,798,837, 4,751,225, EP 0 179 022 or U.K. 2 140 010 as well as U.S. Pat. Nos. 6,096,329 and 6,685,954 (all incorporated herein by reference). Examples of IGRs suitable for use include but are not limited to methoprene, pyriproxyfen, hydroprene, cyromazine, fluazuron, lufenuron, novaluron, pyrethroids, formamidines such as amitraz, 1-(2,6-difluorobenzoyl)-3-(2-fluoro-4-(trifluoromethyl)phenylurea, and novaluron.

In yet another embodiment of the invention, adulticide insecticides and acaricides can also be added to the composition of the invention. These include pyrethrins (which include cinerin I, cinerin II, jasmolin I, jasmolin II, pyrethrin I, pyrethrin II and mixtures thereof) and pyrethroids, and carbamates (which include but are not limited to benomyl, carbanolate, carbaryl, carbofuran, meththiocarb, metolcarb, promacyl, propoxur, aldicarb, butocarboxim, oxamyl, thiocarboxime and thiofanox).

In some embodiments, the compositions of the invention may include one or more antinematodal agents including, but not limited to, active agents in the benzimidazoles, imidazothiazoles, tetrahydropyrimidines, organophosphates class of compounds. In some embodiments, benzimidazoles including, but not limited to, thiabendazole, cambendazole, parbendazole, oxibendazole, mebendazole, flubendazole, fenbendazole, oxfendazole, albendazole, cyclobendazole, febantel, thiophanate and its o,o-dimethyl analogue may be included in the compositions.

In other embodiments, the compositions may include an imidazothiazole compounds including, but not limited to, tetramisole, levamisole and butamisole. In still other embodiments, the compositions of the invention may include tetrahydropyrimidine active agents including, but not limited to, pyrantel, oxantel, and morantel. Suitable organophosphate active agents include, but are not limited to, coumaphos, trichlorfon, haloxon, naftalofos and dichlorvos, heptenophos, mevinphos, monocrotophos, TEPP, and tetrachlorvinphos.

In other embodiments, the compositions may include the antinematodal compounds phenothiazine, piperazine as the neutral compound and in various salt forms, diethylcarbamazine, phenols such as disophenol, arsenicals such as arsenamide, ethanolamines such as bephenium, thenium closylate, and methyridine; cyanine dyes including pyrvinium chloride, pyrvinium pamoate and dithiazanine iodide; isothiocyanates including bitoscanate, suramin sodium, phthalofyne, and various natural products including, but not limited to, hygromycin B, α-santonin and kainic acid.

In other embodiments, the compositions of the invention may include antitrematodal agents. Suitable antitrematodal agents include, but are not limited to, the miracils such as miracil D and mirasan; praziquantel, clonazepam and its 3-methyl derivative, oltipraz, lucanthone, hycanthone, oxamniquine, amoscanate, niridazole, nitroxynil, various bisphenol compounds known in the art including hexachlorophene, bithionol, bithionol sulfoxide and menichlopholan; various salicylanilide compounds including tribromsalan, oxyclozanide, clioxanide, rafoxanide, brotianide, bromoxanide and closantel; triclabendazole, diamfenetide, clorsulon, hetolin and emetine.

Anticestodal compounds may also be advantageously used in the compositions of the invention including, but not limited to, arecoline in various salt forms, bunamidine, niclosamide, nitroscanate, paromomycin and paromomycin II.

In yet other embodiments, the compositions of the invention may include other active agents that are effective against arthropod parasites. Suitable active agents include, but are not limited to, bromocyclen, chlordane, DDT, endosulfan, lindane, methoxychlor, toxaphene, bromophos, bromophosethyl, carbophenothion, chlorfenvinphos, chlorpyrifos, crotoxyphos, cythioate, diazinon, dichlorenthion, diemthoate, dioxathion, ethion, famphur, fenitrothion, fenthion, fospirate, iodofenphos, malathion, naled, phosalone, phosmet, phoxim, propetamphos, ronnel, stirofos, allethrin, cyhalothrin, cypermethrin, deltamethrin, fenvalerate, flucythrinate, permethrin, phenothrin, pyrethrins, resmethrin, benzyl benzoate, carbon disulfide, crotamiton, diflubenzuron, diphenylamine, disulfuram, isobornyl thiocyanato acetate, methroprene, monosulfuram, pirenonylbutoxide, rotenone, triphenyltin acetate, triphenyltin hydroxide, deet, dimethyl phthalate, and the compounds 1,5a,6,9,9a,9b-hexahydro-4-a(4H)-dibenzofurancarboxaldehyde (MGK-11), 2-(2-ethylhexyl)-3a,4,7, 7a-tetrahydro-4,7-methano-1H-isoindole-1,3(2H)dione (MGK-264), dipropyl-2,5-pyridinedicarboxylate (MGK-326) and 2-(octylthio)ethanol (MGK-874).

An antiparasitic agent that can be combined with the compound of the invention to form a composition can be a biologically active peptide or protein including, but not limited to, depsipeptides, which act at the neuromuscular junction by stimulating presynaptic receptors belonging to the secretin receptor family resulting in the paralysis and death of parasites. In one embodiment of the depsipeptide, the depsipeptide is emodepside (see Willson et al., *Parasitology*, January 2003, 126 (Pt 1):79-86).

An insecticidal agent that can be combined with the compound of the invention to form a composition can be a substituted pyridylmethyl derivative compound such as imidacloprid. Agents of this class are described above, and for example, in U.S. Pat. No. 4,742,060 or in EP 0 892 060. It would be well within the skill level of the practitioner to decide which individual compound can be used in the inventive formulation to treat a particular infection of an insect.

In certain embodiments, an insecticidal agent that can be combined with the compositions of the invention is a semicarbazone, such as metaflumizone.

In another embodiment, the compositions of the invention may advantageously include one or more compounds of the isoxazoline class of compounds. These active agents are described in WO 2007/079162, WO 2007/075459 and US 2009/0133319, WO 2007/070606 and US 2009/0143410, WO 2009/003075, WO 2009/002809, WO 2009/024541, WO 2005/085216 and US 2007/0066617 and WO 2008/122375, all of which are incorporated herein by reference in their entirety.

In another embodiment of the invention, nodulisporic acid and its derivatives (a class of known acaricidal, anthelmintic, anti-parasitic and insecticidal agents) may be added to the compositions of the invention. These compounds are used to treat or prevent infections in humans and animals and are described, for example, in U.S. Pat. Nos. 5,399,582, 5,962,499, 6,221,894 and 6,399,786, all of which are hereby incorporated by reference in their entirety. The compositions may include one or more of the known nodulisporic acid derivatives in the art, including all stereoisomers, such as those described in the literature cited above.

In another embodiment, anthelmintic compounds of the amino acetonitrile class (AAD) of compounds such as monepantel (ZOLVIX) and the like may be added to the compositions of the invention. These compounds are described, for example, in WO 2004/024704; Sager et al., Veterinary Parasitology, 2009, 159, 49-54; Kaminsky et al., Nature vol. 452, 13 Mar. 2008, 176-181. The compositions of the invention may also include aryloazol-2-yl cyanoethylamino compounds such as those described in US 2008/0312272 to Soll et al., which is incorporated herein in its entirety, and thioamide derivatives of these compounds, as described in U.S. patent application Ser. No. 12/582,486, filed Oct. 20, 2009, which is incorporated herein by reference.

The compositions of the invention may also be combined with paraherquamide compounds and derivatives of these compounds, including derquantel (see Ostlind et al., *Research in Veterinary Science*, 1990, 48, 260-61; and Ostlind et al., *Medical and Veterinary Entomology*, 1997, 11, 407-408). The paraherquamide family of compounds are known class of compounds that include a spirodioxepino indole core with activity against certain parasites (see *Tet. Lett.* 1981, 22, 135; *J. Antibiotics* 1990, 43, 1380, and *J. Antibiotics* 1991, 44, 492). In addition, the structurally related marcfortine family of compounds, such as marcfortines A-C, are also known and may be combined with the formulations of the invention (see *J. Chem. Soc.—Chem. Comm.* 1980, 601 and *Tet. Lett.* 1981, 22, 1977). Further references to the paraherquamide derivatives can be found, for example, in WO 91/09961, WO 92/22555, WO 97/03988, WO 01/076370, WO 09/004,432, U.S. Pat. No. 5,703,078 and U.S. Pat. No. 5,750,695, all of which are hereby incorporated by reference in their entirety.

In general, the additional active agent is included in a dose of between about 0.1 µg and about 1000 mg. More typically, the additional active agent may be included in a dose of about 10 µg to about 500 mg, about 1 mg to about 300 mg, about 10 mg to about 200 mg or about 10 mg to about 100 mg. In one embodiment of the invention, the additional active agent is included in a dose of between about 1 µg and about 10 mg. In other embodiments of the invention, the additional active agent may be included in a dose of about 5 µg/kg to about 50 mg/kg per weight of the animal. In other embodiments, the additional active agent may be present in a dose of about 0.01 mg/kg to about 30 mg/kg, about 0.1 mg/kg to about 20 mg/kg, or about 0.1 mg/kg to about 10 mg/kg of weight of animal. In other embodiments, the additional active agent may be present in a dose of about 5 µg/kg to about 200 µg/kg or about 0.1 mg/kg to about 1 mg/kg of weight of animal. In still another embodiment of the invention, the additional active agent is included in a dose between about 0.5 mg/kg to about 50 mg/kg.

The proportions, by weight, of the combinations of N-aryl-pyrazole compound/formamidine compound and the additional active agent are for example between about 1/10,000 and about 10,000/1. More typically, the proportions are in a proportion by weight of about 1/100 to about 10,000/1, about 1/1 to about 1,000/1, or about 5/1 to about 10,000/1, or about 5/1 to about 1,000/1. However, one of ordinary skill in the art would be able to select the appropriate ratio of N-aryl-pyrazole compound/substituted imidazole compound and the additional active agent for the intended host and use thereof.

Optionally, a fragrance may be added to any of the compositions of the invention. Fragrances which are useful for the invention include but are not limited to:

(i) carboxylic acid esters such as octyl acetate, isoamyl acetate, isopropyl acetate and isobutyl acetate;

(ii) fragrant oils such as lavender oil.

The compositions of the invention are made by mixing the appropriate amount of N-aryl-pyrazole compound and substituted imidazole compound, veterinarily acceptable solvent and optionally a crystallization inhibitor, film former, odor dissipation enhancer, etc., to form a composition of the invention. Various forms (e.g. tablets, pastes, pour-on, spot-on, collars, etc.) of the composition can be obtained by following the method of making these forms described above by the description of making these forms found in general formulation text known to those in the art, e.g. *Remington—The Science and Practice of Pharmacy* (21$^{st}$ Edition) (2005), *Goodman & Gilman's The Pharmacological Basis of Therapeutics* (11$^{th}$ Edition) (2005) and *Ansel's Pharmaceutical Dosage Forms and Drug Delivery Systems* (8$^{th}$ Edition), edited by Allen et al., Lippincott Williams & Wilkins, (2005).

The inventive formulations may contain other inert ingredients such as antioxidants, preservatives, or pH stabilizers. These compounds are well known in the formulation art. Antioxidant such as an alpha tocopherol, ascorbic acid, ascorbyl palmitate, fumaric acid, malic acid, sodium ascorbate, sodium metabisulfate, n-propyl gallate, BHA (butylated hydroxy anisole), BHT (butylated hydroxy toluene) monothioglycerol and the like, may be added to the present formulation. The antioxidants are generally added to the formulation in amounts of from about 0.01 to about 2.0%, based upon total weight of the formulation, with about 0.05 to about 1.0% being especially preferred. Preservatives, such as the parabens (methylparaben or propylparaben), are suitably used in the formulation in amounts ranging from about 0.01 to about 2.0%, with about 0.05 to about 1.0% being especially preferred. Other preservatives include benzalkonium chloride, benzethonium chloride, benzoic acid, benzyl alcohol, bronopol, butylparaben, cetrimide, chlorhexidine, chlorobutanol, chlorocresol, cresol, ethylparaben, imidurea, methylparaben, phenol, phenoxyethanol, phenylethyl alcohol, phenylmercuric acetate, phenylmercuric borate, phenylmercuric nitrate, potassium sorbate, sodium benzoate, sodium propionate, sorbic acid, thimerosal, and the like. Ranges for these compounds include from about 0.01 to about 5%.

Compounds which stabilize the pH of the formulation are also contemplated. Again, such compounds are well known to a practitioner in the art as well as how to use these compounds. Buffering systems include, for example, systems selected from the group consisting of acetic acid/acetate, malic acid/malate, citric acid/citrate, tataric acid/tartrate, lactic acid/lactate, phosphoric acid/phosphate, glycine/glycimate, tris, glutamic acid/glutamates and sodium carbonate.

The compositions of the invention are administered in antiparasiticidally effective amounts which are determined by the route of administration, e.g. oral, parenteral, topical, etc. In one embodiment of the invention, the compositions of the invention are applied as a pour-on or spot-on formulation.

In each aspect of the invention, the compounds and compositions of the invention can be applied against a single pest or combinations thereof.

The compositions of the invention contain 1-arylpyrazole compounds in combination with a substituted imidazole compound and may be administered continuously, for treatment or prevention, by known methods. In this manner, an effective amount of the compounds is administered to the animal in need thereof. By "effective amount" is intended a sufficient amount of a composition of the invention to eradicate or reduce the number of parasites infesting the animal. Generally, a dose of from about 0.001 to about 100 mg per kg of body weight given as a single dose or in divided doses for a period of from 1 to 5 days will be satisfactory but, of course, there can be instances where higher or lower dosage ranges are indicated, and such are within the scope of this invention. It is well within the routine skill of the practitioner to determine a particular dosing regimen for a specific host and parasite.

In one treatment embodiment, the treatment is carried out so as to administer to the animal, on a single occasion, a dose containing between about 0.001 and about 100 mg/kg of a 1-arylpyrazole compound and a substituted imidazole compound. In another treatment embodiment, the treatment is via a direct topical administration such as a pour-on, ready-to-use, spot-on, spray, etc., type formulation. Higher amounts may be provided for very prolonged release in or on the body of the animal. In another treatment embodiment, the amount of 1-arylpyrazole and substituted imidazole compounds for birds and other animals which are small in size is greater than about 0.01 mg/kg, and in another embodiment for the treatment of small-sized birds and other animals, the amount of 1-aryl-5-alkyl pyrazole compound is between about 1 and about 100 mg/kg of weight of animal.

The solutions according to the invention may be applied using any means known per se, e.g. using an applicator gun or a metering flask.

For the pour-on form of the composition, the volume applied can be of the order of about 0.3 to about 100 mL. In other embodiments, volume applied of the pour-on formulations may be about 1 ml to about 100 ml or about 1 ml to about 50 ml. In still other embodiments, the volume may be about 5 ml to about 50 ml or about 10 ml to about 100 ml.

In another embodiment of the invention, application of a spot-on formulation according to the present invention can also provide long-lasting and broad-spectrum efficacy when the solution is applied to the mammal or bird. The spot-on formulations provide for topical administration of a concentrated solution, suspension, microemulsion or emulsion for intermittent application to a spot on the animal, generally between the two shoulders (solution of spot-on type).

In yet another embodiment, an N-aryl-pyrazole compound and a substituted imidazole compound can be combined in the same solvent system.

The application of an N-aryl-pyrazole compound and a substituted imidazole compound would be expected to have efficacy against a wide range of parasites including fleas, ticks and mites. It was surprising that the application of a 1-arylpyrazole compound and a substituted imidazole compound resulted in synergistic effects with respect to efficacy against ticks.

In one embodiment of the method of use, a composition comprising a 1-arylpyrazole compound and a substituted imidazole compound has an efficacy against ticks of about 80.0% or higher for at least about 43 days. In another embodiment of this method of use, a composition comprising a 1-arylpyrazole compound and a substituted imidazole compound has an efficacy against ticks of about 90.0% or higher for at least about 43 days. In yet another embodiment of the invention, a composition comprising a 1-arylpyrazole compound and a substituted imidazole compound has an efficacy of about 95% or higher for at least about 43 days or longer. In still another embodiment of the invention, a composition comprising a 1-arylpyrazole compound and a substituted imidazole compound has an efficacy of about 96% or higher for at least about 43 days or longer. In each of these embodiments of use against ticks, a further embodiment of the invention is where the 1-arylpyrazole compound is fipronil; the substituted imidazole compound is 1H-imidazole, 2-(2,3-dihydro-4-methyl-1H-inden-1-yl). In another embodiment, the 1-arylpyrazole compound is a 5-alkyl substituted 1-arylpyrazole compound and the substituted imidazole compound is 1H-imidazole, 2-(2,3-dihydro-4-methyl-1H-inden-1-yl).

The synergistic and long-lasting effects of the compositions of the embodiments from the same solvent system for 1-arylpyrazole and for a substituted imidazole make them suitable for once a month (30 days or a calendar month) or once very two months (60 days or two calendar months) application of the composition in its deliverable form.

The animals that can be treated with the compositions of the invention include but are not limited to birds and mammals (either wild or domesticated), e.g., livestock and companion animals such as cats, dogs, horses, chickens, sheep, goats, pigs, turkeys and cattle. In one embodiment of the invention, the mammal is a cat or a dog.

In one embodiment of the location of administration, a single formulation containing the active agent in a substantially liquid carrier and in a form which makes possible a single application, or an application repeated a small number of times, will be administered to the animal over a localized region of the animal, e.g. between the two shoulders. In one embodiment of the invention, the localized region has a surface area of about 10 cm² or larger. In another embodiment of the invention, the localized region has a surface area of between about 5 and about 10 cm² area.

The invention is further described by the following numbered paragraphs:

1. A veterinary formulation for treating or preventing a parasitic infestation in an animal comprising:

(a) a 1-aryl-5-alkyl or 5-haloalkylpyrazole of formula (IA) or a veterinarily acceptable salt thereof,

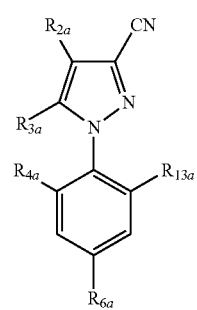

(IA)

wherein:

$R_{2a}$ is $—S(O)_m R_{11a}$;

$R_{3a}$ is methyl, ethyl or $C_1$-$C_4$ haloalkyl;

$R_{4a}$ is halogen;

$R_{6a}$ is $C_1$-$C_4$ alkyl or haloalkyl;

$R_{13a}$ is halogen;

$R_{11a}$ is $C_1$-$C_4$ haloalkyl; and m is 0, 1 or 2;

(b) a substituted imidazole compound of formula (II),

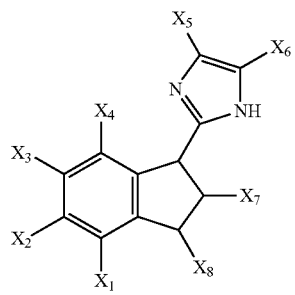

wherein $X_1$, $X_2$, $X_3$, $X_4$, $X_5$, $X_6$, $X_7$ and $X_8$ are defined as in Table 1;
(c) a veterinarily acceptable carrier; and
(d) optionally a crystallization inhibitor.

2. A veterinary formulation for treating or preventing a parasitic infestation in an animal comprising:
(a) a 1-aryl-5-alkyl or 5-haloalkylpyrazole of formula (IB) or a veterinarily acceptable salt thereof,

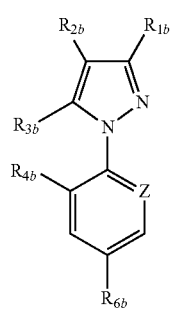

(IB)

wherein:
$R_{1b}$ is alkyl, CN or halogen;
$R_{2b}$ is $S(O)_6 R_{14b}$ or 4,5-dicyanoimidazol-2-yl or haloalkyl;
$R_{14b}$ is alkyl or haloalkyl;
$R_{3b}$ is a hydrogen, halogen, —$NR_{7b}R_{8b}$, —$S(O)_m R_{9b}$, —$C(O)R_{9b}$, —$C(O)OR_{9b}$, alkyl, haloalkyl, —$OR_{10b}$ or an —$N=C(R_{11b})(R_{12b})$;
$R_{6b}$ is a halogen, haloalkyl, haloalkoxy, $S(O)_q CF_3$ or $SF_5$ group;
$R_{7B}$ and $R_{8B}$ independently represent a hydrogen, alkyl, haloalkyl, —C(O)alkyl, —$S(O)_r CF_3$; acyl or alkoxycarbonyl; or
$R_{7b}$ and $R_{8b}$ can together form a divalent alkylene radical which is optionally interrupted by one or two divalent heteroatoms;
$R_{9b}$ is an alkyl or haloalkyl;
$R_{10b}$ is hydrogen, alkyl or haloalkyl;
$R_{11b}$ is hydrogen or alkyl radical;
$R_{12b}$ is an optionally substituted aryl or an optionally substituted heteroaryl group;
$R_{4b}$ and $R_{13b}$ represent, independently of one another, hydrogen, halogen CN or $NO_2$;
m, n, q and r represent, independently of one another, an integer equal to 0, 1 or 2; and Z represents a trivalent nitrogen atom or a C—$R_{13b}$ radical, the three other valencies of the carbon atom forming part of the aromatic ring;
(b) a substituted imidazole compound of formula (II),

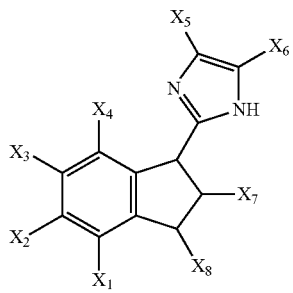

wherein $X_1$, $X_2$, $X_3$, $X_4$, $X_5$, $X_6$, $X_7$ and $X_8$ are defined as in Table 1;
(c) a veterinarily acceptable carrier; and
(d) optionally a crystallization inhibitor.

3. The composition of paragraph 2, wherein:
$R_{1b}$ is methyl, CN or halogen;
$R_{2b}$ is $S(O)_6 R_{14b}$;
$R_{14b}$ is $C_1$-$C_6$-alkyl or $C_1$-$C_6$-haloalkyl;
$R_{3b}$ is —$NR_{7b}R_{8b}$;
$R_{7b}$ and $R_{8b}$ independently represent a hydrogen, $C_1$-$C_6$-alkyl, $C_1$-$C_6$-haloalkyl, —C(O)$C_1$-$C_6$-alkyl, —$S(O)_r CF_3$, $C_1$-$C_6$-acyl or $C_1$-$C_6$-alkoxycarbonyl radical;
$R_{6b}$ is a halogen, $C_1$-$C_6$-haloalkyl, or $C_1$-$C_6$-haloalkoxy;
m, n, q and r represent, independently of one another, an integer equal to 0 or 1; and
Z is a C—$R_{13b}$ radical.

4. The composition of paragraph 2, wherein:
$R_{1b}$ is methyl, CN or halogen;
$R_{2b}$ is $S(O)_n R_{14b}$;
$R_{14b}$ is $C_1$-$C_6$-alkyl or $C_1$-$C_6$-haloalkyl;
$R_{3b}$ is alkyl or haloalkyl;
$R_{6b}$ is a halogen, $C_1$-$C_6$-haloalkyl, or $C_1$-$C_6$-haloalkoxy;
m, n, q and r represent, independently of one another, an integer equal to 0 or 1; and
Z is a C—$R_{13b}$ radical.

5. The composition of paragraph 1 or 2, wherein the veterinarily acceptable carrier comprises acetone, acetonitrile, benzyl alcohol, ethanol, isopropanol, diisobutyl adipate, diisopropyl adipate, butyl diglycol, dipropylene glycol n-butyl ether, ethylene glycol monoethyl ether, ethylene glycol monomethyl ether, dipropylene glycol monomethyl ether, liquid polyoxyethylene glycols, propylene glycol monomethyl ether, propylene glycol monoethyl ether, 2-pyrrolidone, N-methylpyrrolidone, diethylene glycol monoethyl ether, triacetin, butyl acetate, octyl acetate, propylene carbonate, butylene carbonate, dimethyl sulfoxide, an amide, dimethylformamide, dimethylacetamide, or any combination thereof 6. The composition of paragraph 1 or 2, wherein the veterinarily acceptable carrier comprises aryl ethers, alkoxybenzene compounds; aliphatic carboxylic acid esters, aromatic carboxylic acid esters, aliphatic ketones, cyclic ketones, or mixtures thereof 7. The composition of paragraph 1 or 2, wherein the veterinarily acceptable carrier comprises methoxybenzene, butyl acetate, benzyl acetate, methyl isobutyl ketone, ethyl benzoate, benzyl benzoate, octyl acetate, or mixtures thereof 8. The composition of paragraph 1 or 2, wherein the veterinarily acceptable carrier comprises an aprotic solvent with a dielectric constant of about 2 to about 30.

9. The composition of paragraph 8, wherein the at least one aprotic solvent(s) with a dielectric constant of about 2 to about 30 is a $C_1$-$C_{10}$ carboxylic acid ester, a phenyl carboxylic acid ester, a carboxylic acid benzyl ester, a benzoic acid $C_1$-$C_4$ alkyl ester, a $C_1$-$C_6$ saturated aliphatic ketone, or a mixture thereof 10. A composition for the treatment and prevention of a parasitic infestation in an animal comprising the 1-arylpyrazole compound fipronil, the substituted imidazole compound 1H-imidazole, 2-(2,3-dihydro-4-methyl-1H-inden-1-yl); at least one veterinarily acceptable carrier, and optionally a crystallization inhibitor.

11. A composition for the treatment and prevention of a parasitic infestation in an animal comprising the 1-arylpyrazole compound fipronil, the substituted imidazole compound 1H-imidazole, 2-(2,3-dihydro-7-methyl-1H-inden-1-yl); at least one veterinarily acceptable carrier, and optionally a crystallization inhibitor.

12. A method for the treatment or prevention of a parasitic infestation in an animal comprising administering an effective amount of the composition of paragraph 1 or 2 to the animal in need thereof 13. The method of paragraph 12, wherein the 1-arylpyrazole compound(s) and the substituted imidazole compound(s) are administered simultaneously.

14. A veterinary formulation for treating or preventing a parasitic infestation in an animal comprising:
(a) a 1-aryl-5-alkyl or 5-haloalkylpyrazole of formula (IA) or a veterinarily acceptable salt thereof,

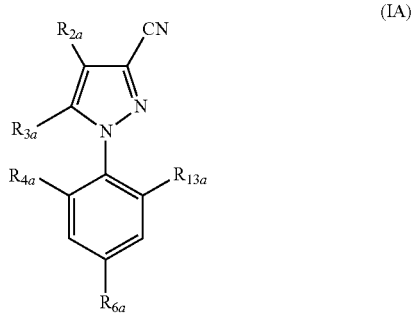

(IA)

wherein:
$R_{2a}$ is —$S(O)_m R_{11a}$;
$R_{3a}$ is methyl, ethyl or $C_1$-$C_4$ haloalkyl;
$R_{4a}$ is halogen;
$R_{6a}$ is $C_1$-$C_4$ alkyl or haloalkyl;
$R_{13a}$ is halogen;
$R_{11a}$ is $C_1$-$C_4$ haloalkyl; and
m is 0, 1 or 2;

(b) at least one substituted imidazole compound of formula (III):

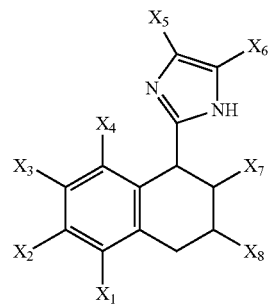

(III)

wherein:
$X_1$, $X_2$, $X_3$, $X_4$, $X_5$, $X_6$, $X_7$ and $X_8$ are as detailed above in Table 2;
(c) a veterinarily acceptable carrier; and
(d) optionally one or more crystallization inhibitors.

15. A veterinary formulation for treating or preventing a parasitic infestation in an animal comprising:
(a) a 1-aryl-5-alkyl or 5-haloalkylpyrazole of formula (IB) or a veterinarily acceptable salt thereof,

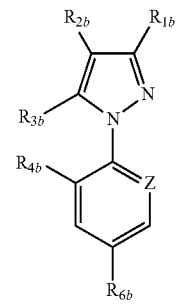

(IB)

wherein:
$R_{1b}$ is alkyl, CN or halogen;
$R_{2b}$ is $S(O)_n R_{14b}$ or 4,5-dicyanoimidazol-2-yl or haloalkyl;
$R_{14b}$ is alkyl or haloalkyl;
$R_{3b}$ is a hydrogen, halogen, —$NR_{7b}R_{8b}$, —$S(O)_m R_{9b}$, —$C(O)R_{9b}$, —$C(O)OR_{9b}$, alkyl, haloalkyl, —$OR_{10b}$ or an —$N=C(R_{11b})(R_{12b})$;
$R_{6b}$ is a halogen, haloalkyl, haloalkoxy, $S(O)_q CF_3$ or $SF_5$ group;
$R_{7B}$ and $R_{8B}$ independently represent a hydrogen, alkyl, haloalkyl, —C(O)alkyl, —$S(O)_r CF_3$, acyl or alkoxycarbonyl; or
$R_{7b}$ and $R_{8b}$ can together form a divalent alkylene radical which is optionally interrupted by one or two divalent heteroatoms;
$R_{9b}$ is an alkyl or haloalkyl;
$R_{10b}$ is hydrogen, alkyl or haloalkyl;
$R_{11b}$ is hydrogen or alkyl radical;
$R_{12b}$ is an optionally substituted aryl or an optionally substituted heteroaryl group;
$R_{4b}$ and $R_{13b}$ represent, independently of one another, hydrogen, halogen CN or $NO_2$;
m, n, q and r represent, independently of one another, an integer equal to 0, 1 or 2; and
Z represents a trivalent nitrogen atom or a C—$R_{13b}$ radical, the three other valencies of the carbon atom forming part of the aromatic ring;

(b) at least one substituted imidazole compound of formula (III):

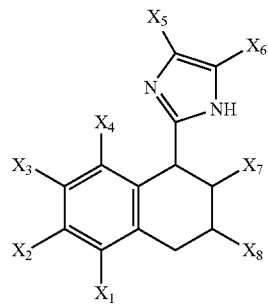

wherein:
$X_1$, $X_2$, $X_3$, $X_4$, $X_5$, $X_6$, $X_7$ and $X_8$ are as detailed above in Table 2;
c) a veterinarily acceptable carrier; and
d) optionally one or more crystallization inhibitors.

16. The composition of paragraph 15, wherein:
$R_{1b}$ is methyl, CN or halogen;
$R_{2b}$ is $S(O)_n R_{14b}$;
$R_{14b}$ is $C_1$-$C_6$-alkyl or $C_1$-$C_6$-haloalkyl;
$R_{3b}$ is —$NR_{7b}R_{8b}$,
$R_{7b}$ and $R_{8b}$ independently represent a hydrogen, $C_1$-$C_6$-alkyl, $C_1$-$C_6$-haloalkyl, —$C(O)C_1$-$C_6$-alkyl, —$S(O)_r CF_3$, $C_1$-$C_6$-acyl or $C_1$-$C_6$-alkoxycarbonyl radical;
$R_{6b}$ is a halogen, $C_1$-$C_6$-haloalkyl, or $C_1$-$C_6$-haloalkoxy;
m, n, q and r represent, independently of one another, an integer equal to 0 or 1; and
Z is a C—$R_{13b}$ radical.

17. The composition of paragraph 2, wherein:
$R_{1b}$ is methyl, CN or halogen;
$R_{2b}$ is $S(O)_n R_{14b}$;
$R_{14b}$ is $C_1$-$C_6$-alkyl or $C_1$-$C_6$-haloalkyl;
$R_{3b}$ is alkyl or haloalkyl;
$R_{6b}$ is a halogen, $C_1$-$C_6$-haloalkyl, or $C_1$-$C_6$-haloalkoxy;
m, n, q and r represent, independently of one another, an integer equal to 0 or 1; and
Z is a C—$R_{13b}$ radical.

18. The composition of paragraphs 14 or 15, wherein the veterinarily acceptable carrier comprises acetone, acetonitrile, benzyl alcohol, ethanol, isopropanol, diisobutyl adipate, diisopropyl adipate, butyl diglycol, dipropylene glycol n-butyl ether, ethylene glycol monoethyl ether, ethylene glycol monomethyl ether, dipropylene glycol monomethyl ether, liquid polyoxyethylene glycols, propylene glycol monomethyl ether, propylene glycol monoethyl ether, 2-pyrrolidone, N-methylpyrrolidone, diethylene glycol monoethyl ether, triacetin, butyl acetate, octyl acetate, propylene carbonate, butylene carbonate, dimethyl sulfoxide, an amide, dimethylformamide, dimethylacetamide, or any combination thereof 19. The composition of paragraph 14 or 15, wherein the veterinarily acceptable carrier comprises aryl ethers, alkoxybenzene compounds; aliphatic carboxylic acid esters, aromatic carboxylic acid esters, aliphatic ketones, cyclic ketones, or mixtures thereof 20. The composition of paragraph 14 or 15, wherein the veterinarily acceptable carrier comprises methoxybenzene, butyl acetate, benzyl acetate, methyl isobutyl ketone, ethyl benzoate, benzyl benzoate, octyl acetate, or mixtures thereof 21. The composition of paragraph 14 or 15, wherein the veterinarily acceptable carrier comprises an aprotic solvent with a dielectric constant of about 2 to about 30.

22. The composition of paragraph 21, wherein the at least one aprotic solvent(s) with a dielectric constant of about 2 to about 30 is a $C_1$-$C_{10}$ carboxylic acid ester, a phenyl carboxylic acid ester, a carboxylic acid benzyl ester, a benzoic acid $C_1$-$C_4$ alkyl ester, a $C_1$-$C_6$ saturated aliphatic ketone, or a mixture thereof 23. A composition for the treatment and prevention of a parasitic infestation in an animal comprising the 1-arylpyrazole compound fipronil, the substituted imidazole compound 2-(5,6-dimethyl-1,2,3,4-tetrahydronaphthalen-1-yl)-1H-imidazole; at least one veterinarily acceptable carrier, and optionally a crystallization inhibitor.

24. A method for the treatment or prevention of a parasitic infestation in an animal comprising administering an effective amount of the composition of paragraph 23 to the animal in need thereof 25. The method of paragraph 24, wherein the 1-arylpyrazole compound(s) and the substituted imidazole compound(s) are administered simultaneously.

Having thus described in detail various embodiments of the present invention, it is to be understood that the invention defined by the above paragraphs is not to be limited to particular details set forth in the above description as many apparent variations thereof are possible without departing from the spirit or scope of the present invention.

What is claimed is:

1. A veterinary formulation for treating or preventing a parasitic infestation in an animal comprising:
(a) a 1-aryl-5-alkyl or 5-haloalkylpyrazole of formula (IA) or a veterinarily acceptable salt thereof,

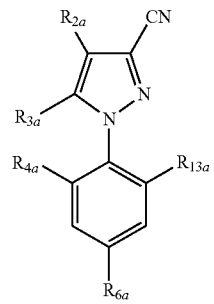

wherein:
$R_{2a}$ is —$S(O)_m R_{11a}$;
$R_{3a}$ is methyl, ethyl or $C_1$-$C_4$ haloalkyl;
$R_{4a}$ is halogen;
$R_{6a}$ is $C_1$-$C_4$ alkyl or haloalkyl;
$R_{13a}$ is halogen;
$R_{11a}$ is $C_1$-$C_4$ haloalkyl; and
m is 0, 1 or 2;

(b) a substituted imidazole compound of formula (II),

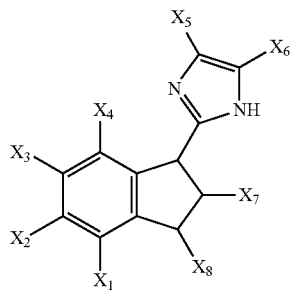

wherein
$X_1$ is H, Cl, or $CH_3$;
$X_2$ and $X_8$ are H;
$X_3$ is H, F, —$OCH_3$, Cl, I, —$OCHF_2$, —$OCF_3$, $NH_2$, $CHCH_2$, $CHCHCH_3$, CCH, $CCCH_3$, $C_2H_5$ or $CH_3$;
$X_4$, $X_5$, $X_6$ and $X_7$ are H or $CH_3$;
(c) a veterinarily acceptable carrier; and
(d) optionally a crystallization inhibitor.

2. A veterinary formulation for treating or preventing a parasitic infestation in an animal comprising:
(a) a 1-aryl-5-alkyl or 5-haloalkylpyrazole of formula (IB) or a veterinarily acceptable salt thereof,

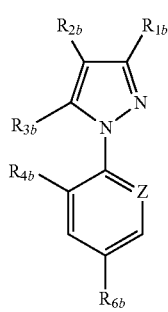

(IB)

wherein:
$R_{1b}$ is alkyl, CN or halogen;
$R_{2b}$ is $S(O)_6R_{14b}$ or 4,5-dicyanoimidazol-2-yl or haloalkyl;
$R_{14b}$ is alkyl or haloalkyl;
$R_{3b}$ is a hydrogen, halogen, —$NR_{7b}R_{8b}$, —$S(O)_mR_{9b}$, —$C(O)R_{9b}$, —$C(O)OR_{9b}$, alkyl, haloalkyl, —$OR_{10b}$ or an —N=$C(R_{11b})(R_{12b})$;
$R_{6b}$ is a halogen, haloalkyl, haloalkoxy, $S(O)_qCF_3$ or $SF_5$ group;
$R_{7B}$ and $R_{8B}$ independently represent a hydrogen, alkyl, haloalkyl, —C(O)alkyl, —$S(O)_rCF_3$, acyl or alkoxycarbonyl; or
$R_{7b}$ and $R_{8b}$ can together form a divalent alkylene radical which is optionally interrupted by one or two divalent heteroatoms;
$R_{9b}$ is an alkyl or haloalkyl;
$R_{10b}$ is hydrogen, alkyl or haloalkyl;
$R_{11b}$ is hydrogen or alkyl radical;
$R_{12b}$ is an optionally substituted aryl or an optionally substituted heteroaryl group;
$R_{4b}$ and $R_{13b}$ represent, independently of one another, hydrogen, halogen CN or $NO_2$;
m, n, q and r represent, independently of one another, an integer equal to 0, 1 or 2; and Z represents a trivalent nitrogen atom or a C—$R_{13b}$ radical, the three other valencies of the Carbon atom forming part of the aromatic ring;
(b) a substituted imidazole compound of formula (II),

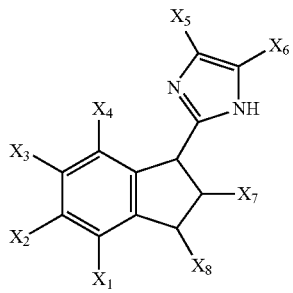

wherein
$X_1$ is H, Cl, or $CH_3$;
$X_2$ and $X_8$ are H;
$X_3$ is H, F, —$OCH_3$, Cl, I, —$OCHF_2$, —$OCF_3$, $NH_2$, $CHCH_2$, $CHCHCH_3$, CCH, $CCCH_3$, $C_2H_5$ or $CH_3$;
$X_4$, $X_5$, $X_6$ and $X_7$ are H or $CH_3$;
(c) a veterinarily acceptable carrier; and
(d) optionally a crystallization inhibitor.

3. The composition of claim 2, wherein:
$R_{1b}$ is methyl, CN or halogen;
$R_{2b}$ is $S(O)_6R_{14b}$;
$R_{14b}$ is $C_1$-$C_6$-alkyl or $C_1$-$C_6$-haloalkyl;
$R_{3b}$ is —$NR_{7b}R_{8b}$;
$R_{7b}$ and $R_{8b}$ independently represent a hydrogen, $C_1$-$C_6$-alkyl, $C_1$-$C_6$-haloalkyl, —$C(O)C_1$-$C_6$-alkyl, —$S(O)_rCF_3$, $C_1$-$C_6$-acyl or $C_1$-$C_6$-alkoxycarbonyl radical;
$R_{6b}$ is a halogen, $C_1$-$C_6$-haloalkyl, or $C_1$-$C_6$-haloalkoxy;
m, n, q and r represent, independently of one another, an integer equal to 0 or 1; and
Z is a C—$R_{13b}$ radical.

4. The composition of claim 2, wherein:
$R_{1b}$ is methyl, CN or halogen;
$R_{2b}$ is $S(O)_nR_{14b}$;
$R_{14b}$ is $C_1$-$C_6$-alkyl or $C_1$-$C_6$-haloalkyl;
$R_{3b}$ is alkyl or haloalkyl;
$R_{6b}$ is a halogen, $C_1$-$C_6$-haloalkyl, or $C_1$-$C_6$-haloalkoxy;
m, n, q and r represent, independently of one another, an integer equal to 0 or 1; and
Z is a C—$R_{13b}$ radical.

5. The composition of claim 1 or 2, wherein the veterinarily acceptable carrier comprises acetone, acetonitrile, benzyl alcohol, ethanol, isopropanol, diisobutyl adipate, diisopropyl adipate, butyl diglycol, dipropylene glycol n-butyl ether, ethylene glycol monoethyl ether, ethylene glycol monomethyl ether, dipropylene glycol monomethyl ether, liquid polyoxyethylene glycols, propylene glycol monomethyl ether, propylene glycol monoethyl ether, 2-pyrrolidone, N-methylpyrrolidone, diethylene glycol monoethyl ether, triacetin, butyl acetate, octyl acetate, propylene carbonate, butylene carbonate, dimethyl sulfoxide, an amide, dimethylformamide, dimethylacetamide, or any combination thereof.

6. The composition of claim 1 or 2, wherein the veterinarily acceptable carrier comprises aryl ethers, alkoxybenzene compounds; aliphatic carboxylic acid esters, aromatic carboxylic acid esters, aliphatic ketones, cyclic ketones, or mixtures thereof.

7. The composition of claim 1 or 2, wherein the veterinarily acceptable carrier comprises methoxybenzene, butyl acetate, benzyl acetate, methyl isobutyl ketone, ethyl benzoate, benzyl benzoate, octyl acetate, or mixtures thereof.

8. The composition of claim 1 or 2, wherein the veterinarily acceptable carrier comprises an aprotic solvent with a dielectric constant of about 2 to about 30.

9. The composition of claim 8, wherein the at least one aprotic solvent(s) with a dielectric constant of about 2 to about 30 is a $C_1$-$C_{10}$ carboxylic acid ester, a phenyl carboxylic acid ester, a carboxylic acid benzyl ester, a benzoic acid $C_1$-$C_4$ alkyl ester, a $C_1$-$C_6$ saturated aliphatic ketone, or a mixture thereof.

10. A composition for the treatment and prevention of a parasitic infestation in an animal comprising the 1-arylpyrazole compound fipronil, the substituted imidazole compound 1H-imidazole, 2-(2,3-dihydro-4-methyl-1H-inden-1-yl); at least one veterinarily acceptable carrier, and optionally a crystallization inhibitor.

11. A method for the treatment or prevention of a parasitic infestation in an animal comprising administering an effective amount of the composition of claim 1 or 2 to the animal in need thereof.

12. The method of claim 11, wherein the 1-arylpyrazole compound(s) and the substituted imidazole compound(s) are administered simultaneously.

13. The composition of claim 11, wherein the veterinarily acceptable carrier comprises acetone, acetonitrile, benzyl alcohol, ethanol, isopropanol, diisobutyl adipate, diisopropyl adipate, butyl diglycol, dipropylene glycol n-butyl ether, ethylene glycol monoethyl ether, ethylene glycol monomethyl ether, dipropylene glycol monomethyl ether, liquid polyoxyethylene glycols, propylene glycol monomethyl ether, propylene glycol monoethyl ether, 2-pyrrolidone, N-methylpyrrolidone, diethylene glycol monoethyl ether, triacetin, butyl acetate, octyl acetate, propylene carbonate, butylene carbonate, dimethyl sulfoxide, an amide, dimethylformamide, dimethylacetamide, or any combination thereof.

14. The composition of claim 2, wherein the veterinarily acceptable carrier comprises aryl ethers, alkoxybenzene compounds; aliphatic carboxylic acid esters, aromatic carboxylic acid esters, aliphatic ketones, cyclic ketones, or mixtures thereof.

15. The composition of claim 2, wherein the veterinarily acceptable carrier comprises methoxybenzene, butyl acetate, benzyl acetate, methyl isobutyl ketone, ethyl benzoate, benzyl benzoate, octyl acetate, or mixtures thereof.

16. The composition of claim 2, wherein the veterinarily acceptable carrier comprises an aprotic solvent with a dielectric constant of about 2 to about 30.

* * * * *